(12) United States Patent
Tachas

(10) Patent No.: US 11,976,281 B2
(45) Date of Patent: May 7, 2024

(54) THERAPEUTIC USES AND METHODS

(71) Applicant: Antisense Therapeutics Ltd, Victoria (AU)

(72) Inventor: George Tachas, Victoria (AU)

(73) Assignee: Antisense Therapeutics Ltd, Toorak (AU)

( * ) Notice: Subject to any disclaimer, the term of this patent is extended or adjusted under 35 U.S.C. 154(b) by 45 days.

(21) Appl. No.: 16/404,561

(22) Filed: May 6, 2019

(65) Prior Publication Data

US 2020/0095587 A1 Mar. 26, 2020

Related U.S. Application Data

(63) Continuation-in-part of application No. PCT/AU2018/051353, filed on Dec. 18, 2018.

(30) Foreign Application Priority Data

May 4, 2018 (AU) .................................. 2018901531

(51) Int. Cl.
| | | |
|---|---|---|
| *C12N 15/113* | (2010.01) | |
| *A61K 31/573* | (2006.01) | |
| *A61K 31/58* | (2006.01) | |
| *A61P 21/00* | (2006.01) | |

(52) U.S. Cl.
CPC ........ *C12N 15/1138* (2013.01); *A61K 31/573* (2013.01); *A61K 31/58* (2013.01); *A61P 21/00* (2018.01); *C12N 2310/11* (2013.01); *C12N 2310/313* (2013.01); *C12N 2310/321* (2013.01); *C12N 2310/3341* (2013.01); *C12N 2320/31* (2013.01)

(58) Field of Classification Search
CPC ............ C12N 15/1138; C12N 2310/11; C12N 2310/321; C12N 2310/3341; A61P 21/00
See application file for complete search history.

(56) References Cited

U.S. PATENT DOCUMENTS

| | | |
|---|---|---|
| 8,759,314 B2 | 6/2014 | Klinger et al. |
| 8,765,700 B2 | 7/2014 | Tachas et al. |
| 2012/0046342 A1* | 2/2012 | Van Deutekom ....... A61P 29/00 514/44 A |
| 2012/0258093 A1* | 10/2012 | Butler-Browne ........................... G01N 33/56972 424/133.1 |
| 2013/0345293 A1* | 12/2013 | Klinger ............... C12N 15/1138 514/44 R |

FOREIGN PATENT DOCUMENTS

| | | |
|---|---|---|
| JP | 2011-525531 | 9/2011 |
| WO | WO 2005/070921 A1 | 8/2005 |
| WO | WO 2010/008474 A2 | 1/2010 |
| WO | WO 2011/020874 A1 | 2/2011 |
| WO | WO 2012/034194 A1 | 3/2012 |
| WO | WO 2017/075670 A1 | 5/2017 |

OTHER PUBLICATIONS

Monaco and Major (Expert Rev Clin Immunol . Jan. 2012;8(1):63-72), abstract only (Year: 2012).*
Seferian et al., (PLoS One 10(2): e0113999, 2015) (Year: 2015).*
Altschul et al., "Basic Local Alignment Search Tool," J. Mol. Biol. (1990) 215:403-410.
Elbashir et al., "Duplexes of 21±nucleotide RNAs mediate RNA interference in cultured mammalian cells", Nature (2001a) 411:494-498.
Elbashir et al., "RNA interference is mediated by 21-and 22-nucleotide RNAs" Genes Dev. (2001b) 15:188-200.
Englisch et al., "Chemically Modified Oligonucleotides as Probes and Inhibitors", Angewandte Chemie, International Edition (1991) 30:613.
Fire et al., "Potent and specific genetic interference by double-stranded RNA in *Caenorhabditis elegans*", Nature (1998) 391:806-811.
Grounds MD, "Visions & Reflections (Minireview)—Two-tiered hypotehtes for Duchenne muscular dystrophy", *Cell. Mol. Life. Sci.* 2008.
Guo and Kempheus, "par-1, a Gene Required for Establishing Polarity in C. elegans Embryos, Encodes a Putative Ser/Thr Kinase That Is Asymmetrically Distributed" Cell (1995) 81:611-620.
Limmroth et al., "CD49d antisense drug ATL1102 reduces disease activity in patients with relapsing-remitting MS", American Academy of Neurology 83 Nov. 11, 2014.
Limmroth, V et al, "CD49d antisense drug ATL1102 reduces disease activity in patients with relapsing-remitting MS", Neurology, 2014, vol. 83, pp. 1780-1788.
Montgomery et al., "RNA as a target of double-stranded RNA-mediated genetic interference in *Caenorhabditis elegans*", Proc. Natl. Acad. Sci. USA. (1998) 95:15502-15507.
Nielsen et al., "Sequence-Selective Recognition of DNA by Strand Displacement with a Thymine-Substituted Polyamide", Science (1991) 254, 1497-1500.
Pinto-Mariz F et al "CD49d is a disease progression biomarker and a potential target for immunotherapy in Duchene muscular dystrophy" Skeletal Muscle, 2015, vol. 5, Article 45, pp. 1-10.
Rosenberg et al. "Immune-mediated pathology in Duchenne muscular dystrophy", *Sci Transl Med* 2015, 7: 299rv4.
Savino, W et al. "Flow Cytometry-Defined D49d Expression in Circulating T-Lymphocytes is a Biomarker for Disease Progression in Duchene Muscular Dystrophy", Methods in Molecular Biology, vol. 1687, Duchenne Muscular Dystrophy: Methods and Protocols—Chapter 16, pp. 219-227.
Tabara et al., "RNAi in *C. elegans*: Soaking in the Genome Sequence", Science (1998) 282:430-431.

(Continued)

*Primary Examiner* — Richard A Schnizer
(74) *Attorney, Agent, or Firm* — Knobbe, Martens, Olson & Bear, LLP

(57) ABSTRACT

The specification discloses a method of treating muscular disorders such as muscular dystrophy comprising periodically administering an inhibitory oligonucleotide to human CD49d ((the alpha 4 chain of VLA-4).

13 Claims, 5 Drawing Sheets

Specification includes a Sequence Listing.

(56) References Cited

OTHER PUBLICATIONS

Tijsterman et al., "RNA Helicase MUT-14-Depenendent Gene Silencing Triggered in *C. elegans* by Short Antisense RNAs", Science (2002) 295:694-697.
Tilley, J.W., "VLA-4 antagonists", Expert Opinion on Therapeutic Patents, s00s, vol. 12, No. 7, pp. 991-1008, 2002.
Timmons and Fire, "Specific interference by ingested dsRNA" Nature (1998) 395:854.
Tuschl et al., "Targeted mRNA degradation by double-stranded RNA in vitro", Genes Dev. (1999) 13:3191-3197.
Wan et al., "Synthesis, biophysical properties and biological activity of second generation antisense oligonucleotides containing chiral phosphorothioate linkages", Nucleic Acids Research (2014) 42 (22):13456-13468.
Zhang and Madden, "PowerBLAST: A New Network BLAST Application for Interactive or Automated Sequence Analysis and Annotation" Genome Res. (1997) 7:649-656.
Ducharte, et al., "A Novel CD49d Targeting Antisense, ATL1102, Effectively Mobilizes Acute Myeloid Leukemia Cells", Blood, American Society of Hematology, vo. 126(23), p. 3807, 2015.
Tachas, et al., "P.284 ATL1102 treatment improves PUL2.0 in non-ambulant boys with Duchenne muscular dystrophy compared to a natural history control", *Abstract/Neuromuscular Disorders 30* (2020) S46-S150.
Extended European Search Report dated Jan. 20, 2022 for European Patent Application No. 18917201.8.
Office Action dated Dec. 19, 2022 for Japanese Patent Application No. 2021-510492.
Office Action dated Jun. 9, 2023 for Canadian Patent Application No. 3,098,912.

\* cited by examiner

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: methylcytosine
<222> LOCATION: (1)..(1)
<220> FEATURE:
<221> NAME/KEY: 2'-O-(2-methoxyethyl) modified ribonucleosides
<222> LOCATION: (1)..(3)
<220> FEATURE:
<221> NAME/KEY: methyluracil
<222> LOCATION: (2)..(2)
<220> FEATURE:
<221> NAME/KEY: 2'deoxyribonucleosides
<222> LOCATION: (4)..(13)
<220> FEATURE:
<221> NAME/KEY: methylcytosine
<222> LOCATION: (7)..(7)
<220> FEATURE:
<221> NAME/KEY: methyluracil
<222> LOCATION: (13)..(13)
<220> FEATURE:
<221> NAME/KEY: methylcytosine
<222> LOCATION: (14)..(14)
<220> FEATURE:
<221> NAME/KEY: 2'-O-(2-methoxyethyl) modified ribonucleosides
<222> LOCATION: (14)..(20)
<220> FEATURE:
<221> NAME/KEY: methylcytosine
<222> LOCATION: (15)..(15)
<220> FEATURE:
<221> NAME/KEY: methyluracil
<222> LOCATION: (17)..(17)
<220> FEATURE:
<221> NAME/KEY: methyluracil
<222> LOCATION: (18)..(18)
<220> FEATURE:
<221> NAME/KEY: methylcytosine
<222> LOCATION: (19)..(19)
<220> FEATURE:
<221> NAME/KEY: methyluracil
<222> LOCATION: (20)..(20)

<400> SEQUENCE: 1
cugagtctgt ttccauucu                                                  20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide
<220> FEATURE:
```

```
<221> NAME/KEY: 2'-O-(2-methoxyethyl) modified ribonucleosides
<222> LOCATION: (1)..(5)
<220> FEATURE:
<221> NAME/KEY: 2'deoxyribonucleosides
<222> LOCATION: (6)..(15)
<220> FEATURE:
<221> NAME/KEY: methylcytosine
<222> LOCATION: (9)..(9)
<220> FEATURE:
<221> NAME/KEY: methylcytosine
<222> LOCATION: (10)..(10)
<220> FEATURE:
<221> NAME/KEY: methylcytosine
<222> LOCATION: (12)..(12)
<220> FEATURE:
<221> NAME/KEY: methylcytosine
<222> LOCATION: (13)..(13)
<220> FEATURE:
<221> NAME/KEY: 2'-O-(2-methoxyethyl) modified ribonucleosides
<222> LOCATION: (16)..(20)
<220> FEATURE:
<221> NAME/KEY: methylcytosine
<222> LOCATION: (18)..(18)
<220> FEATURE:
<221> NAME/KEY: methylcytosine
<222> LOCATION: (19)..(19)
<220> FEATURE:
<221> NAME/KEY: methylcytosine
<222> LOCATION: (20)..(20)

<400> SEQUENCE: 2
atatttttcc acctgtgccc                                                   20

<210> SEQ ID NO 3
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 3
acagtgtacc tccttttctc                                                   20
```

THERAPEUTIC USES AND METHODS

CROSS-REFERENCE TO RELATED APPLICATIONS

This application is a continuation-in-part of International Application No. PCT/AU2018/051353, filed on Dec. 18, 2018, which claims the benefit of Australian Provisional Application No. 2018901531, filed on May 4, 2018, and this application is a continuation-in-part of and claims the benefit of Australian Provisional Application No. 2018901531, filed on May 4, 2018, the disclosures of each of which are incorporated herein by reference in their entireties, including any drawings.

SEQUENCE LISTING

The present application is being filed along with a Sequence Listing in electronic format. The Sequence Listing is provided as a file entitled FBRIC67_005P1.txt created May 6, 2019, which is approximately 2.11 Kb in size. The information in the electronic format of the sequence listing is incorporated herein by reference in its entirety.

FIELD OF DISCLOSURE

The present specification enables compositions and methods for treating muscular disorders such as muscular dystrophy.

BACKGROUND ART

Bibliographic details of references in the subject specification are also listed at the end of the specification.

Reference to any prior art in this specification is not, and should not be taken as, acknowledgement or any form of suggestion that this prior art forms part of the common general knowledge in any country.

Muscular Dystrophy (MD) is a group of disorders characterized by progressive weakness and wasting of specific muscle tissue (myonecrosis) and replacement of skeletal muscles with fibrous, bony or fatty tissue. There are several different forms of muscular dystrophy affecting either males or males and females, many of which appear during infancy and childhood up to middle age or later. The form and severity vary with age of onset in particular, with younger subjects often experiencing acute progressive disease.

The most common forms of MD are Duchene muscular dystrophy (DMD), limb girdle muscular dystrophy (LGMD), Becker muscular dystrophy (BMD), congenital muscular dystrophy (CMD including Fukuyama Type congenital MD and congenital MD with myosin deficiency, fascioscapulohumeral, oculopharyngeal, Emery-Dreifuss, and distal forms. Almost all types of MD arise from single-gene mutations.

DMD and BMD involve a defect in the dystrophin gene on the X-chromosome. The dystrophin protein serves to link the contractile machinery (actin filaments) of the muscle cell (sarcomeres) and the cytoskeleton with the extracellular matrix (ECM) where collagens transmit the muscle force (Grounds MD, 2008). The ECM is known to play a complex role in muscle function and muscle regeneration. Dystrophic myofibres are associated with necrosis, inflammation and fibrosis. The precise sequence of events leading to progressive disease as a result of dystrophin deficiency is not understood at the molecular level. Children with DMD have dystrophin deficient muscles and are susceptible to contraction induce injury to muscles that triggers the immune system which exacerbates muscles damage as summarized in a publication by the Direct of the FDA CDER (Rosen et al, 2015). Ongoing deterioration in muscle strength affects lower limbs leading to impaired mobility, and also affects upper limbs, leading to further loss of function and self-care ability. While gene therapy and exon skipping approaches would be ideal, researchers are also focused on understanding the nature of the disease in order to develop strategies and agents able to ameliorate its severity and delay its progression. The mdx mouse model is widely employed to investigate mechanisms and interventions pre-clinically. Grounds MD, 2008, identified the need for a two tiered approach to target both chronic and acute phases of the disease in mdx mice.

DMD is a devastating condition which affects mainly boys with an incidence of about 1:3,500 live births. Boys may lose their ability to walk at an early age and become wheelchair bound typically post-pubescent, and death often from cardiopulmonary compromise frequently occurs in the $3^{rd}$ decade of life. BMD is similar to DMD but much milder.

Current treatments with corticosteroids are aimed at reducing the severity of the disease by reducing inflammation to maintain muscle mass and function for a period of time. Corticosteroids have an acute anti-inflammatory effect which can be short term and their mechanism of action is not understood. They are less than optimal because side effects severely limit their use, and they may also cause atrophy. Prednisolone at 0.75 mg/kg/day and Deflazacort 0.9 mg/kg/day are standard therapies for ambulant DMD patients but when boys become non-ambulant there is no consensus as to the benefits of CS, and boys may stay on treatment, sometimes the fixed dose they were on when they lost ambulation, which is a reduced mg/kg/day dose or they may come off CS treatment. Edasalonexent in as an anti-inflammatory NF-kappa B drug undergoing development as a monotherapy in young ambulant boys with DMD. There are several drugs in clinical trials targeting the different aspects of dystrophy. For example, Tamoxifen targets fibrosis, Idebenone respiratory function and Ataluren for stop codon skipping are undergoing clinical trials for MD. Oligonucleotide therapy for DMD by inducing targeted exon skipping of dystrophin gene has been assessed with mixed results. Eteplirsen, a morpholino oligonucleotide has progressed to a confirmatory study in the 13% of DMD children with a genetic stop codon mutation in exon 51 amenable to exon 51 skipping whilst Drisapersen, a 2'-O-methyl phosphorothioate oligonucleotide for exon 51 skipping failed to achieve activity and FDA approval.

These deficiencies in current therapy suggest the need for additional therapeutic approaches.

SUMMARY OF THE DISCLOSURE

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the singular forms "a", "an" and "the" include plural aspects unless the context clearly dictates otherwise. Thus, for example, reference to "a composition" includes a single composition, as well as two or more compositions; reference to "an agent" includes one agent, as well as two or more agents; reference to "the disclosure" includes single and multiple aspects of the disclosure and so forth.

In one embodiment, the present disclosure provides methods for treatment of muscular dystrophy in a subject comprising administering an inhibitory oligonucleotide to human CD49d ((the alpha 4 chain of VLA-4).

In one embodiment, exemplary inhibitory oligonucleotides include isolated or synthetic antisense RNA or DNA, iRNA, siRNA or siDNA, miRNA, miRNA mimics, shRNA or DNA and antisense DNA or RNA or DNA:RNA hybrids.

In one embodiment, the present disclosure provides a method of treating muscular dystrophy in a subject in need thereof, the method comprising periodically administering to the subject a pharmaceutical composition comprising a pharmaceutically acceptable carrier and a therapeutically effective amount of an oligonucleotide comprising the structure:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO. 1) wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}$C),
or a pharmaceutically acceptable salt thereof.

In one embodiment, administration is for a time and under conditions sufficient to improve one or more markers, signs or symptoms of muscular dystrophy or to delay progression of muscular dystrophy in a subject.

In one embodiment, administration is for a time and under conditions sufficient to improve one or more markers, signs or parameters of muscle performance or function, or limb performance or function in the subject. Reference herein to muscle performance includes motor performance and includes attributes such as strength/force power, endurance and muscle length as well as limb function. All such attributes may be assessed using art recognised methods including those described or referred to herein.

In one embodiment, administration is for a time and under conditions sufficient to improve one or more markers, signs or parameters of muscle performance, or to delay progression or the rate of progression of one or more markers, signs or parameters of muscle performance including strength, power, endurance, muscle length in the subject.

In one embodiment, administration is in combination with standard corticosteroid treatment.

In one embodiment, corticosteroid is administered at a low dose. Reference to a low dose corticosteroid includes $\frac{2}{3}^{rd}$, $\frac{1}{2}$, $\frac{1}{4}$, and a $\frac{1}{3}^{rd}$ of the standard dose. In one embodiment, corticosteroid is administered at a low dose. Reference to a low dose corticosteroid includes $\frac{4}{5}^{th}$, $\frac{3}{4}^{th}$, $\frac{2}{3}^{rd}$, $\frac{1}{2}$, $\frac{1}{3}^{rd}$, $\frac{1}{4}$, and a $\frac{1}{5}^{th}$ of the standard dose. In another embodiment the corticosteroid dose is 10, 20, 30, 40, 50, 60, 70 mg/kg/day oral prednisolone, or 10, 20, 40, 40, 50, 60, 70 or 80 mg of deflazacort.

In one embodiment, administration of inhibitory oligonucleotide is therapeutically effective in the presence of a standard or a low dose of corticosteroid.

In one embodiment, administration of antisense oligonucleotide is therapeutically effective in the absence of corticosteroid.

In one embodiment, administration of antisense oligonucleotide is therapeutically effective in the absence of corticosteroid and wherein the subject is ambulant.

In one embodiment, administration of antisense oligonucleotide is therapeutically effective in the absence of corticosteroid and wherein the subject is non-ambulant.

In one embodiment, the present disclosure provides methods for modifying muscle performance comprising contacting muscle cells or tissues with an inhibitory oligonucleotide to human CD49d ((the alpha 4 chain of VLA-4).

Muscle cells or tissues may be contacted ex vivo, topically or in vivo.

In one embodiment, the contacting is by administration of inhibitory oligonucleotide to a subject in need thereof in order to increase muscle performance or delay or reduce the rate of progression of muscular dystrophy.

In one embodiment, the muscle performance modified includes increased muscle strength, and or increased muscle function.

In one embodiment, increased muscle strength is increased eccentric contraction. Eccentric contraction is contraction while lengthening muscle fibres which is critical in walking and the controlled and pain free movement of limbs.

In one embodiment therefore, the description enables a method for improving muscle function such as limb function or delaying decline in muscle function such as limb function in a subject with muscular dystrophy, the method comprising periodically administering to the subject a pharmaceutical composition comprising a pharmaceutically acceptable carrier and a therapeutically effective amount of an oligonucleotide comprising the structure:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO. 1) wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}$C),
or a pharmaceutically acceptable salt or stereoisomer thereof, for a time and under conditions sufficient improve muscle function such as limb function in a subject.

In another embodiment, the description enables a method for improving muscle performance such as muscle or limb strength or delaying decline in muscle performance such as muscle or limb strength in a subject with muscular dystrophy, the method comprising periodically administering to the subject a pharmaceutical composition comprising a pharmaceutically acceptable carrier and a therapeutically effective amount of an oligonucleotide comprising the structure:

5'-$^{Me}$C$^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO. 1) wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;

d) the nucleotides at the positions 13 to 20 from the 5' end are 2'-O-(2-methoxyethyl) modified ribonucleosides; and e) all cytosines are 5-methylcytosines ($^{Me}C$), or a pharmaceutically acceptable salt or stereoisomer thereof, for a time and under conditions sufficient to improve muscle performance such as muscle (e.g., limb) strength or delay decline in muscle performance such as muscle (e.g. limb) strength.

In one embodiment, the oligonucleotide is an RNA-DNA hybrid.

In one embodiment, the subject is non-ambulatory due to MD.

In one embodiment, the subject is post-pubescent.

In one embodiment the method includes monitoring for CD4+ and/or CD8+ T cell levels. In one embodiment the method includes monitoring for reduced CD4+ and/or CD8+ T cell levels. In one embodiment, the method includes monitoring for M1 macrophages or HLADR$^+$ monocytes. In one embodiment, the method includes monitoring for reduced M1 macrophages or HLADR+ monocytes.

In one embodiment, the method comprises determining the level or presence of one or more markers of MD or dystrophic myofibres include the level or number of immune cells or immunomodulatory factors produced thereby, the level of inflammatory markers or the level of markers of fibrosis or the level of markers of muscle status.

In one embodiment, the one or more markers of MD or MD progression or dystrophic myofibres include the level or number of immune cells or immunomodulatory factors produced thereby, the level of inflammatory markers or the level of markers of fibrosis In one embodiment, markers of muscle performance or the level of markers of muscle status include muscle strength, power, endurance, and length function.

Markers of muscle status include without limitation markers of motor muscle function, markers indicative of muscle fibrosis or the absence thereof, markers indicative of muscle degeneration or regeneration, markers of cardiac function and markers of pulmonary function.

In one embodiment the improving one or more signs of MD or dystrophic myofibres includes improved limb function, body muscle function, cardiac and/or lung function.

In one embodiment, the method comprises determining the level or presence of one or more signs of MD or dystrophic myofibres. Illustrative signs include limb function, body muscle function, cardiac and lung function.

In one embodiment, the one or more symptoms of MD or dystrophic myofibres include quality of life factors such as energy levels, happiness, perceived ease of walking, upper limb function activities etc.

In one embodiment, the subject in need thereof includes subjects with a genetic and/or clinical diagnosis of MD and relatively low levels of dystrophic myofibres and inflammatory markers.

In one embodiment, the subject displays normal or only slightly elevated levels of inflammatory cells. Inflammatory cells include T cells (CD4, CD8), B-cells (CD-19), granulocytes, (neutrophils, basophils, and eosinophils).

In one embodiment, the subject displays normal or only slightly elevated levels of CD49d cells.

In one embodiment, the subject displays normal or only slightly elevated levels of CD49d T cells.

In one embodiment, the subject displays normal or only slightly elevated levels of immune cell markers such as CD3, CD4, CD8, CD49d, CD29 and HLA-DR.

Suitable methods of marker including cell or protein/nucleic acid or lipid analysis are known in the art and include without limitation flow cytometry, bead technologies and ELISA-based methods, chromatographic and/or MS methods, hybridization or sequencing based methods.

In a further embodiment, the subject diagnosed with MD displays significantly elevated or acute levels of severely dystrophic myofibres accompanied by severe muscle necrosis and inflammation.

In one embodiment, the subject displays significantly elevated levels of CD49d T-cells relative to normal healthy controls.

In one embodiment, the form of MD in a subject is selected from the group consisting of Duchene muscular dystrophy (DMD), limb girdle muscular dystrophy (LGMD), Becker muscular dystrophy (BMD), congenital muscular dystrophy (CMD including Fukuyama Type congenital MD and congenital MD with myosin deficiency), fascioscapulohumeral, oculopharyngeal, Emery-Dreifuss, and distal muscular dystrophy.

In one embodiment, the subject has DMD or BMD and is non-ambulatory.

In one embodiment, the subject has DMD or BMD and is post-pubescent.

In another form of the present disclosure, embodiments are contemplated directed to; pharmaceutical compositions when used in the presently described methods or uses, uses of the herein described compositions in the manufacture of a medicament for the treatment or prevention of a muscular dystrophy in a subject, pharmaceutical compositions for use in the presently described methods.

Accordingly, in one embodiment, the present disclosure provides for the use of an oligonucleotide comprising the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO. 1) wherein, a) each of the 19 internucleotide linkages of the oligonucleotide is an O,O-linked phosphorothioate diester;

b) the nucleotides at the positions 1 to 3 from the 5' end are 2'-O-(2-methoxyethyl) modified ribonucleosides;

c) the nucleotides at the positions 4 to 12 from the 5' end are 2'-deoxyribonucleosides;

d) the nucleotides at the positions 13 to 20 from the 5' end are 2'-O-(2-methoxyethyl) modified ribonucleosides; and e) all cytosines are 5-methylcytosines ($^{Me}C$), or a pharmaceutically acceptable salt or stereoisomer thereof, in the manufacture of a medicament for the treatment or prevention of muscular dystrophy or to delay progression of muscular dystrophy in a subject.

Accordingly, in one embodiment, the present disclosure provides for the use of an oligonucleotide comprising the structure:

5'-$^{Me}C^{Me}$UG AGT $^{Me}$CTG TTT $^{Me}U^{Me}C^{Me}$C A$^{Me}U^{Me}$U $^{Me}C^{Me}$U-3' (SEQ ID NO. 1) wherein, a) each of the 19 internucleotide linkages of the oligonucleotide is an O,O-linked phosphorothioate diester;

b) the nucleotides at the positions 1 to 3 from the 5' end are 2'-O-(2-methoxyethyl) modified ribonucleosides;

c) the nucleotides at the positions 4 to 12 from the 5' end are 2'-deoxyribonucleosides;

d) the nucleotides at the positions 13 to 20 from the 5' end are 2'-O-(2-methoxyethyl) modified ribonucleosides; and e) all cytosines are 5-methylcytosines ($^{Me}C$), or a pharmaceutically acceptable salt or stereoisomer thereof, in the manufacture of a medicament to enhance muscle performance in a subject in need thereof.

Accordingly, in one embodiment, the present disclosure provides for the use of an oligonucleotide comprising the structure:

5'-$^{Me}C^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO. 1) wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}$C), or a pharmaceutically acceptable salt or stereoisomer thereof, in the manufacture of a medicament to enhance muscle performance, maintain muscle performance, or reduce the rate of decline in muscle performance in a subject in need thereof.

In one embodiment, muscle performance is muscle function or measured using known estimators of muscle function.

In one embodiment, muscle performance is muscle strength or measured using known estimators of muscle strength.

In one embodiment, modified or enhanced performance is enhanced or increased ability to conduct eccentric muscle contractions as described in the examples.

In another embodiment, the description enables an oligonucleotide comprising the structure:

5'-$^{Me}C^{Me}$UG AGT $^{Me}$CTG TTT $^{Me}$U$^{Me}$C$^{Me}$C A$^{Me}$U$^{Me}$U $^{Me}$C$^{Me}$U-3' (SEQ ID NO. 1) wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}$C), or a pharmaceutically acceptable salt or stereoisomer thereof, for use in the treatment or prevention or to delay progression of muscular dystrophy in a subject.

In one embodiment, the present disclosure enables a method of treating muscular dystrophy in a subject in need thereof, the method comprising periodically administering to the subject a therapeutically effective amount of an inhibitory oligonucleotide to human CD49d to improve one or more markers, signs or symptoms of muscular dystrophy or to delay progression of muscular dystrophy in a subject.

In one embodiment, administration of antisense oligonucleotide is in combination with or an adjunctive treatment with standard or low dose corticosteroid treatment.

In one embodiment, corticosteroid is administered at a low dose.

In one embodiment, administration of antisense oligonucleotide is effective in the absence of corticosteroid therapy.

In another embodiment, there is disclosed a use of an inhibitory oligonucleotide to human CD49d in the preparation of a medicament for improving one or more markers, signs or symptoms of muscular dystrophy or to delay progression of muscular dystrophy in a subject with muscular dystrophy.

In one embodiment, there is provided a pharmaceutical composition comprising an inhibitory oligonucleotide to human CD49d for use in treating muscular dystrophy or delaying the progression of muscular dystrophy in a subject.

The above summary is not and should not be seen in any way as an exhaustive recitation of all embodiments of the present disclosure.

Many modifications will be apparent to those skilled in the art without departing from the scope of the present disclosure.

BRIEF DESCRIPTION OF THE FIGURES

The accompanying drawings, which are incorporated into and form a part of the specification, illustrate several embodiments of the present invention and, together with the description, serve to explain the principles of the invention.

KEY TO SEQUENCE LISTING

Figure 1A:
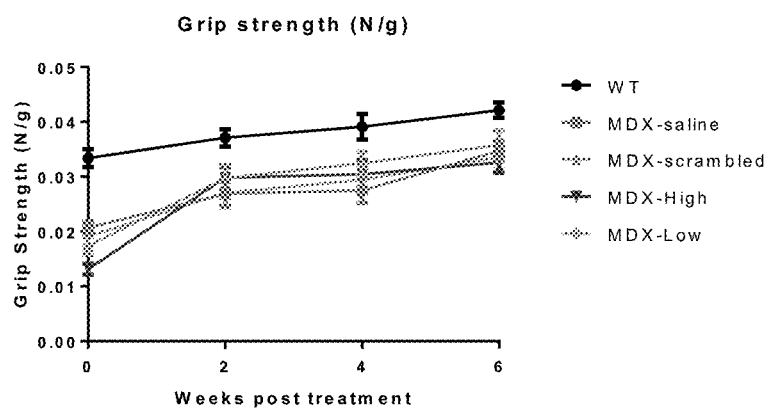
FIGS. 1A and 1B are a graphical representation of data illustrating the Grip strength at baseline and over the 6 weeks of treatment (mean and SEM) for test and control mice.

SEQ ID NO: 1 human α4 integrin antisense compound (ATL1102)
SEQ ID NO: 2 murine α4 integrin antisense compound (ISIS348574)
SEQ ID NO: 3: negative control for SEQ ID NO:2 (ISIS358342)

DETAILED DISCUSSION OF PARTICULAR EMBODIMENTS

The subject disclosure is not limited to particular screening procedures for agents, specific formulations of agents and various medical methodologies, as such may vary. Unless defined otherwise, all technical and scientific terms used herein have the same meanings as commonly understood by one of ordinary skill in the art to which this disclosure belongs. Any materials and methods similar or equivalent to those described herein can be used to practice or test the present disclosure. Practitioners are particularly directed to and Ausubel et al., Current Protocols in Molecular Biology, Supplement 47, John Wiley & Sons, New York, 1999; Colowick and Kaplan, eds., Methods In Enzymology, Academic Press, Inc.; Weir and Blackwell, eds., Handbook of Experimental Immunology, Vols. I-IV, Blackwell Scientific Publications, 1986; Remington's Pharmaceutical Sciences ($18^{th}$ ed., Mack Easton, Pa. (1990)); Hogarth et al. Nature Communications 8:14143, 2017, Garton et al. The American Journal of Human Genetics 102, 845-857, 2018, for definitions and terms of the art and other methods known to the person skilled in the art.

The term "subject" includes a human subject or individual diagnosed with MD or a clinical study model animal, DMD, for example is often clinically diagnosed when infant motor milestones are delayed at 18 months. Early features of muscle weakness include a wide based gait, toe walking hyperlordosis of the spine, frequent falls, hypertrophy of muscles, such as the calf, deltoid, quadriceps, tongue masseters, difficulty getting up, arm weakness. Loss of ambulation typically occurs between 7 and 13 years of age in DMD, while later ambulation is characteristic of BMD. Cardiopulmonary deficits may also be apparent. Fatigue and speech development may also be delayed. However, no upper motor neurone signs or muscle fasciculation is observed.

Diagnosis of DMD may be confirmed by dystrophin immunofluorescence testing and/or immunoblot showing dystrophin deficiency, and a clinical picture consistent with typical DMD. Alternatively, gene deletions test positive (missing one or more exons) of the dystrophin gene, where reading frame can be predicted as 'out-of-frame', and a clinical picture consistent with typical DMD is indicative. In one embodiment, complete dystrophin gene sequencing may show a point mutation, duplication, or other mutation resulting in a stop codon mutation that can be definitely associated with DMD. A positive family history of DMD confirmed by one of the criteria listed above in a sibling or maternal uncle is also useful. Also used are assessments of DMD characteristic clinical symptoms or signs (e.g., proximal muscle weakness, Gowers' manoeuvre, elevated serum creatinine kinase level).

Suitable improved markers, signs and symptoms of MD or dystrophic myofibres/improved muscle function will be known to those of skill in the art.

Suitable tests include those for increased motor, muscle, cardiac, blood flow, lung function over time during treatment.

In subjects with pre-clinical cardiomyopathy, cardiac efficacy based on serum biomarker response may be determined. This may be achieved by determining the levels of one or more markers such as myostatin ratio, cardiac troponins, cardiac BNP etc. eGFR changes may also be monitored. Other cardiac functions may be assessed by telemetry or rhythm abnormalities assessed by continuous mobile telemetry monitoring.

Further tests include testing for muscle oxygenation parameters and mitochondrial phenotype.

Reduced fibrosis may be assessed by MRI. Reduced muscle fat, reduced cardiac fibrosis, increased pinch strength, grip strength, improved cardiac and lung function tests. Other assessments look for a slowing in the rate of decline of the above functions.

Quality of life questionnaires are very useful in determining the effect of treatments.

Clinical outcomes may involve, for example, determining the percent change in normalized upper extremity reachable surface area, the percent change in cardiac circumferential strain by MRI, cardiac lateral and posterior wall strain is assessed.

Another useful test is to measure forced vital capacity, delayed loss of respiratory function, such as change in FVC 5p from baseline by spirometry measurements.

Motor function tests include determining the mean change in 4 standard stairs climb test before and after treatment, time to rise form floor, magnetic resonance spectroscopy mean change in fat fraction of vastus lateralis muscle at MRS, muscle testing of quadriceps, knee extensor peak torque measurement, ultrasound muscle microvascular blood supply to forearm.

Important clinical assessments include time to walk/run 6 or 10 meters, time to climb 4 stairs, time to descend 4 stairs, time to stand from supine position. Changes in weight, height, BMI may also be assessed.

Alternatively or in addition biomarkers from muscle biopsy assessments, pharmacodynamics markers measuring change in plasma biomarker panel measured by ELISA or proteomics, or change in circulating immune cell markers are assessed.

The term "antisense compound" as used herein refers to an oligomeric compound that hybridizes to a nucleic acid molecule encoding the α4 integrin chain of VLA-4 (α4β1) and/or α4β7 integrin. The α4 integrin chain in humans is CD49d. The antisense compound may interfere with expression of CD49d, β1 integrin and/or β7 integrin.

The term "nucleic acid molecule encoding alpha4 integrin" as used herein encompasses DNA encoding the α4 integrin chain of VLA-4 or α4β7 integrin, RNA (including pre-mRNA and mRNA or portions thereof) transcribed from such DNA, and further, cDNA derived from such RNA.

The term "VLA-4" as used herein refers to a heterodimer of an α4 integrin and a β1 integrin. VLA-4 is expressed at substantial levels on normal peripheral blood B and T cells, thymocytes, monocytes, and other cells, as well as on hematopoietic stem and progenitor cells. VLA-4 is also expressed on mesenchymal and endothelial progenitor cells and mesenchymal stem cells and potentially endothelial stem cells. Ligands for VLA-4 include vascular cell adhesion molecule-1 (VCAM-1) and CS-1, an alternately spliced domain within the Hep II region of fibronectin.

The term "α4β7 integrin" as used herein refers to a heterodimer of an α4 integrin and a β7 integrin. α4β7 integrin identifies a subset of memory T cells with a tropism for the intestinal tract. α4β7 integrin and is also expressed on a subset of mast, lymphocyte and NK progenitor cells. α4β7 integrin is expressed on some stem and progenitor cells. Ligands for α4β7 integrin include MAdCam-1 and VCAM-1.

Nucleic Acids

The present disclosure encompasses use of various oligonucleotides which are also referred to as nucleic acids. Exemplary nucleic acids include DNA (e.g., complementary DNA (cDNA), genomic DNA (gDNA)), RNA (e.g., message RNA (mRNA), short hairpin RNA (shRNA), iRNA, short inhibitory RNA (siRNA), ribosomal RNA (rRNA), tRNA, microRNA, DNA or RNA analogues (e.g., containing base analogues, sugar analogues and/or a non-native backbone and the like), RNA/DNA hybrids and polyamide nucleic acids (PNAs), all of which can be in single- or double-stranded form. In an example, the nucleic acid is isolated. As used herein, the term "isolated nucleic acid" means a nucleic acid that is altered or removed from the natural state through human intervention.

The term "oligonucleotide" broadly means a short nucleic acid molecule. Oligonucleotides readily bind, in a sequence-specific manner, to their respective complementary oligonucleotides, DNA, or RNA to form duplexes. In one embodiment, oligonucleotides are five, six, seven, eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides or more in length.

In one embodiment, oligonucleotides of the present disclosure are inhibitory oligonucleotides. In an example, the term "inhibitory oligonucleotide" refers to any oligonucleotide that reduces the production, expression or biological activity of one or more proteins. For example, an inhibitory oligonucleotide can interfere with translation of mRNA into protein in a ribosome. In another example, an inhibitory oligonucleotide can be sufficiently complementary to either a gene or a mRNA encoding one or more proteins to bind to (hybridize with) a targeted gene(s) or mRNA thereby reducing expression or biological activity of the target protein. In another example, an inhibitory oligonucleotide inhibits the biological activity of an intracellular nucleic acid that does not code for a protein. For example, an inhibitory oligonucleotide can inhibit the biological activity of a non-coding RNA.

The term "antisense" as used herein means a sequence of nucleotides complementary to and therefore capable of binding to a coding sequence, which may be either that of the strand of a DNA double helix that undergoes transcription, or that of a messenger RNA molecule. Antisense DNA is the non-coding strand complementary to the coding strand in double-stranded DNA.

The terms "short hairpin RNA" or "shRNA" refer to an RNA structure having a duplex region and a loop region.

The term small interfering RNA (siRNA), sometimes known as short interfering RNA or silencing RNA, is a class of double-stranded or single stranded RNA molecules, about 19-25 base pairs in length. A siRNA that inhibits or prevents translation to a particular protein is indicated by the protein name coupled with the term siRNA. Typically, a siRNA in various embodiments is a double-stranded or single stranded nucleic acid molecule having about 19 to about 28 nucleotides (i.e. about 19, 20, 21, 22, 23, 24, 25, 26, 27, or 28 nucleotides). "iRNA" refers to an agent that contains RNA and which mediates the targeted cleavage of an RNA transcript via an RNA-induced silencing complex (RISC) pathway. The term "double-stranded RNA" or "dsRNA," as used herein, includes an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above. The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

The term "microRNA" (abbreviated miRNA) is a small non-coding RNA molecule (containing about 22 nucleotides) found in plants, animals and some viruses, that functions in RNA silencing and post-transcriptional regulation of gene expression. The prefix "miR" is followed by a dash and a number, the latter often indicating order of naming. Different miRNAs with nearly identical sequences except for one or two nucleotides are annotated with an additional lower case letter. Numerous miRNAs are known in the art (miRBase V.21 nomenclature; see Kozomara et al. 2013; Griffiths-Jones, S. 2004). Sequences of these miRNAs are well known in the art and may be found, for example, on the world wide web at mirbase dot org.

In one embodiment, "inhibitory oligonucleotides" mimic the activity of one or more miRNA. The term "miRNA mimic", as used herein, refers to small, double-stranded RNA molecules designed to mimic endogenous mature miRNA molecules when introduced into cells. miRNA mimics can be obtained from various suppliers such as Sigma Aldrich and Thermo Fisher Scientific.

In embodiment, "inhibitory oligonucleotides" inhibit the activity of one or more miRNA. Various miRNA species are suitable for this purpose. Examples include, without limitation, antagomirs, interfering RNA, ribozymes, miRNA sponges and miR-masks. The term "antagomir" is used in the context of the present disclosure to refer to chemically modified antisense oligonucleotides that bind to a target miRNA and inhibit miRNA function by preventing binding of the miRNA to its cognate gene target. Antagomirs can include any base modification known in the art. In an example, the above referenced miRNA species are about 10 to 50 nucleotides in length. For example, antagomirs can have antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In one embodiment, the miRNA species are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids.

In one embodiment, nucleic acids encompassed by the present disclosure are synthetic. The term "synthetic nucleic acid" means that the nucleic acid does not have a chemical structure or sequence of a naturally occurring nucleic acid. Synthetic nucleotides include an engineered nucleic acid molecule. In another example, the nucleic acid structure can also be modified into a locked nucleic acid (LNA) with a methylene bridge between the 2' Oxygen and the 4' carbon to lock the ribose in the 3'-endo (North) conformation in the A-type conformation of nucleic acids (Lennox et al 2011; Bader et al 2011). In the context of miRNAs, this modification can significantly increase both target specificity and hybridization properties of the molecule.

Nucleic acids for use in the methods disclosed herein can be designed using routine methods as required. For example, in the context of inhibitory oligonucleotides, target segments of 5, 6, 7, 8, 9, 10 or more nucleotides in length comprising a stretch of at least five (5) consecutive nucleotides within the seed sequence, or immediately adjacent thereto, are considered to be suitable for targeting a gene. Exemplary target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the nucleic acid contains about 5 to about 30 nucleotides). In another example, target segments are represented by RNA sequences that comprise at least the 5 consecutive nucleotides from the 3'-terminus of one of the seed sequence (the remaining nucleotides being a consecutive stretch of the same RNA beginning immediately downstream of the 3'-terminus of the target segment and continuing until the nucleic acid contains about 5 to about 30 nucleotides). The term "seed sequence" is used in the context of the present disclosure to refer to a 6-8 nucleotide (nt) long substring within the first 8 nt at the 5-end of the miRNA (i.e., seed sequence) that is an important determinant of target specificity. Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target nucleic acid sequences), to give the desired effect.

Antisense Compounds to α4 Integrin

In one embodiment the methods of the present disclosure rely on the use of an antisense compound to α4 integrin. Such antisense compounds are targeted to nucleic acids encoding the α4 integrin chain of VLA-4 (α4β1) or α4β7 integrin. In one embodiment, the antisense compound is an oligonucleotide. However, other oligomeric antisense compounds, including but not limited to oligonucleotide mimetics are contemplated.

Hybridization of an antisense compound with its target nucleic acid is generally referred to as "antisense". Hybridization of the antisense compound with its target nucleic acid inhibits the function of the target nucleic acid. Such "antisense inhibition" is typically based upon hydrogen bonding-based hybridization of the antisense compound to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

"Hybridization" as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

A "nucleoside" is a base-sugar combination. The base portion of the nucleoside is normally a heterocyclic base. The two most common classes of such heterocyclic bases are the purines and the pyrimidines. "Nucleotides" are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar.

"Specifically hybridizable" and "complementary" are terms which are used to indicate a sufficient degree of complementarity such that stable and specific binding occurs between the antisense compound and target nucleic acid. It is understood that the antisense compound need not be 100% complementary to its target nucleic acid sequence to be specifically hybridizable. An antisense compound is specifically hybridizable when binding of the antisense compound to the target nucleic acid interferes with the normal function of the target molecule to cause a loss of activity, and there is a sufficient degree of complementarity to avoid non-specific binding of the antisense compound to non-target sequences under conditions in which specific binding is desired, for example, under physiological conditions in the case of therapeutic treatment.

"Complementary" as used herein, refers to the capacity for precise pairing between a nucleobase of the antisense compound and the target nucleic acid. For example, if a nucleobase at a certain position of the antisense compound is capable of hydrogen bonding with a nucleobase at a certain position of the target nucleic acid, then the position of hydrogen bonding between the antisense compound and the target nucleic acid is considered to be a complementary position. The antisense compound may hybridize over one or more segments, such that intervening or adjacent segments are not involved in the hybridization event (e.g., a loop structure or hairpin structure). In one embodiment, the antisense compound comprises at least 70% sequence complementarity to a target region within the target nucleic acid.

For example, an antisense compound in which 18 of 20 nucleobases are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other, or to complementary nucleobases. As such, an antisense compound which is 18 nucleobases in length having 4 noncomplementary nucleobases which are flanked by 2 regions of complete complementarity with the target nucleic acid would have 77.8% overall complementarity with the target nucleic acid and would thus, fall within the scope of the present disclosure. Percent complementarity of an antisense compound with a region of a target nucleic acid can be determined routinely using BLAST programs (basic local alignment search tools) and PowerBLAST programs known in the art (Altschul et al., 1990; Zhang and Madden, 1997).

Antisense Oligonucleotides

The present disclosure provides inter alia antisense oligonucleotides for inhibiting expression of α4 integrin, and/ or VLA-4 and/or α4β7 integrin. Such antisense oligonucleotides are targeted to nucleic acids encoding the α4 integrin chain of VLA-4 or α4β7 integrin.

The term "inhibits" as used herein means any measurable decrease (e.g., 10%, 20%, 50%, 90%, or 100%) in VLA-4 or α4β7 integrin expression. The term "inhibitory nucleotide" means herein an oligonucleotide as described herein which induces any measurable decrease (e.g., 10%, 20%, 50%, 90%, or 100%) in VLA-4 or α4β7 integrin expression As used herein, the term "oligonucleotide" refers to an oligomer or polymer of RNA or DNA or mimetics, chimeras, analogs and homologs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

The oligonucleotides may contain chiral (asymmetric) centers or the molecule as a whole may be chiral. The individual stereoisomers (enantiomers and diastereoisomers) and mixtures of these are within the scope of the present disclosure. Reference may be made to Wan et al. *Nucleic Acids Research* 42 (22:13456-13468, 2014 for a disclosure of antisense oligonucleotides containing chiral phosphorothioate linkages. For a general description of ASO reference may be made to Scoles et al Antisesne Oligonucleotides Neurology Genetics April 2019; 5 (2) DOI: doi.org/10.1212/NXG.000000000000032. In forming oligonucleotides, phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

Antisense oligonucleotides of the disclosure include, for example, ribozymes, siRNA, external guide sequence (EGS) oligonucleotides, alternate splicers, primers, probes, and other oligonucleotides which hybridize to at least a portion of the target nucleic acid. Antisense oligonucleotides of the disclosure may be administered in the form of single stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H therefore results in cleavage of the RNA target, thereby greatly enhancing the efficiency of oligonucleotide-mediated inhibition of gene expression. Similar roles have been postulated for other ribonucleases, such as those in the RNase III and ribonuclease L family of enzymes.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing. The first evidence that dsRNA could lead to gene silencing in animals came in 1995 from work in the nematode, *Caenorhabditis elegans* (Guo and Kempheus, 1995). Montgomery et al. (1998) have shown that the primary interference effects of dsRNA are posttranscriptional. The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., 1998). Recently, it has been shown that it is, in fact, the single-stranded RNA oligomers of antisense polarity of the dsRNAs which are the potent inducers of RNAi (Tijsterman et al., 2002).

A person having ordinary skill in the art could, without undue experimentation, identify antisense oligonucleotides useful in the methods of the present disclosure.

Modified Internucleoside Linkages (Backbones)

Antisense compounds of the present disclosure include oligonucleotides having modified backbones or non-natural internucleoside linkages. Oligonucleotides having modified backbones include those that retain a phosphorus atom in the backbone and those that do not have a phosphorus atom in the backbone.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, that is, a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808, 4,469,863, 4,476,301, 5,023,243, 5,177,196, 5,188,897, 5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, US 5,194,599, U.S. Pat. Nos. 5,565,555, 5,527,899, 5,721,218, 5,672,697 and 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, 5,792,608, 5,646,269 and 5,677,439.

In the phosphorodiamidate morpholino (PMO), the phosphodiester (PO) linkages in the oligonucleotide backbone are replaced with nonionic phosphorodiamidate linkages leading to resistance to PO. Other ASO types have PS modifications that result in resistance to a broad spectrum of nucleases, support RNase H activity, and increase protein binding, which also improves tissue uptake. Morpholinos are aldo oligonucleotides with unique modifications to the ribose sugar that lead to greater target affinity and facilitate nuclease avoidance.

Phosphorothiote (PS) ASOs are usually stereorandom with regard to chiral PS centers, each of which has 2 distinct stereochemical configurations, making two stereoisoforms (Rp and Sp) possible for a 20mer ASO with 19 linkages. In one embodiment, the oligonucleotide is a Rp sterioisoform. In one embodiment, the oligonucleotide is a Sp sterioisoform.

Modified Sugar and Internucleoside Linkages

Antisense compounds of the present disclosure include oligonucleotide mimetics where both the sugar and the internucleoside linkage (i.e. the backbone), of the nucleotide units are replaced with novel groups. The nucleobase units are maintained for hybridization with the target nucleic acid. An oligonucleotide mimetic that has been shown to have excellent hybridization properties is referred to as a peptide nucleic acid (PNA). In PNA compounds, the sugar-backbone of an oligonucleotide is replaced with an amide containing backbone, in particular, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262. Further teaching of PNA compounds can be found in Nielsen et al., 1991.

The antisense compounds of the present disclosure also include oligonucleotides with phosphorothioate backbones and oligonucleotides with heteroatom backbones, for example, —CH2-NH—O—CH2-, —CH2-N(CH3)-O—CH2- [known as a methylene (methylimino) or MMI backbone], —CH2-O—N(CH3)-CH2-, —CH2-N(CH3)-N(CH3)-CH2- and —O—N(CH3)-CH2-CH2- [wherein the native phosphodiester backbone is represented as —O—P—O—CH2-] of U.S. Pat. No. 5,489,677, and the amide backbones of U.S. Pat. No. 5,602,240.

The antisense compounds of the present disclosure also include oligonucleotides having morpholino backbone structures of U.S. Pat. No. 5,034,506.

Modified Sugars

Antisense compounds of the present disclosure include oligonucleotides having one or more substituted sugar moieties.

Examples include oligonucleotides comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl.

In one embodiment, the oligonucleotide comprises one of the following at the 2' position: O[(CH2)nO]mCH3, O(CH2)nOCH3, O(CH2)nNH2, O(CH2)nCH3, O(CH2)nONH2, and O(CH2)nON[(CH2)nCH3]2, where n and m are from 1 to about 10.

Further examples include of modified oligonucleotides include oligonucleotides comprising one of the following at the 2' position: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment, the modification includes 2'-methoxyethoxy (2'-O—CH2CH2OCH3 (also known as 2'-O-(2-methoxyethyl) or 2'-MOE) (Martin et al., 1995), that is, an alkoxyalkoxy group. In a further embodiment, the modification includes 2'-dimethylaminooxyethoxy, that is, a O(CH2)2ON(CH3)2 group (also known as 2'-DMAOE), or 2'-dimethylaminoethoxyethoxy (also known in the art as 2'-O-dimethyl-amino-ethoxy-ethyl or 2'-DMAEOE), that is, 2'-O—CH2-O—CH2-N(CH3)2.

Other modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of the 5' terminal nucleotide.

Oligonucleotides may also have sugar mimetics, such as cyclobutyl moieties in place of the pentofuranosyl sugar.

Representative United States patents that teach the preparation of such modified sugar structures include, but are not limited to, U.S. Pat. Nos. 4,981,957, 5,118,800, 5,319,080, 5,359,044, 5,393,878, 5,446,137, 5,466,786, 5,514,785, 5,519,134, 5,567,811, 5,576,427, 5,591,722, 5,597,909, 5,610,300, U.S. Pat. Nos. 5,627,053, 5,639,873, 5,646,265, 5,658,873, 5,670,633, 5,792,747, and 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene (—CH2-)n group bridging the 2' oxygen atom and the 4' carbon atom, wherein n is 1 or 2. LNAs and preparation thereof are described in WO 98/39352 and WO 99/14226.

Natural and Modified Nucleobases

The present disclosure include oligonucleotides having nucleobase modifications or substitutions. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—CC—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines, such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3', 2': 4,5]pyrrolo[2,3-d]pyrimidin-2-one).

Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in J. I. Kroschwitz (editor), The Concise Encyclopedia of Polymer Science and Engineering, pages 858-859, John Wiley and Sons (1990), those disclosed by Englisch et al. (1991), and those disclosed by Y. S. Sanghvi, Chapter 15: Antisense Research and Applications, pages 289-302, S. T. Crooke, B. Lebleu (editors), CRC Press, 1993.

Certain of these nucleobases are particularly useful for increasing the binding affinity of the oligonucleotide. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 □C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. Nos. 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, 5,681,941 and 5,750,692.

Conjugates

Oligonucleotide compounds of the present disclosure may be conjugated to one or more moieties or groups which enhance the activity, cellular distribution or cellular uptake of the antisense compound.

These moieties or groups may be covalently bound to functional groups such as primary or secondary hydroxyl groups.

Exemplary moieties or groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes.

Moieties or groups that enhance the pharmacodynamic properties include those that improve uptake, enhance resistance to degradation, and/or strengthen sequence-specific hybridization with the target nucleic acid.

Moieties or groups that enhance the pharmacokinetic properties include those that improve uptake, distribution, metabolism or excretion of the compounds of the present disclosure. Representative moieties or groups are disclosed in PCT/US92/09196 and U.S. Pat. No. 6,287,860. Moieties or groups include but are not limited to lipid moieties such as a cholesterol moiety, cholic acid, a thioether, for example, hexyl-S-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Chimeric Compounds

As would be appreciated by those skilled in the art, it is not necessary for all positions in a given compound to be uniformly modified and in fact, more than one of the aforementioned modifications may be incorporated in a single oligonucleotide or even at a single nucleoside within an oligonucleotide.

Compounds of the disclosure include chimeric oligonucleotides. "Chimeric oligonucleotides" contain two or more chemically distinct regions, each made up of at least one monomer unit, that is, a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and if necessary, associated nucleic acid hybridization techniques known in the art.

Chimeric antisense compounds of the disclosure may be formed as composite structures of two or more oligonucleotides, modified oligonucleotides, and/or oligonucleotide mimetics. Such compounds have also been referred to in the art as hybrids or gapmers. Representative United States patents that teach the preparation of such hybrid structures include, but are not limited to, U.S. Pat. Nos. 5,013,830, 5,149,797, 5,220,007, 5,256,775, 5,366,878, 5,403,711, 5,491,133, 5,565,350, 5,623,065, 5,652,355, 5,652,356, and 5,700,922.

Exemplary Oligonucleotides

Illustrative antisense platforms known in the art include without limitation, morpholino, 1gen oligos, $2^{nd}$ gen oligo's, gapmer, siRNA, LNA, BNA, or oligo mimetics like Peptide Nucleic acids. Oligonucleotides may be naked or formulated in liposomes. Oligonucleotides may be linked to a delivery means to cells or not. Oligonucleotides may use an endosome release agent or not.

In one embodiment, the antisense compound is a second generation phosphorothioate backbone 2'-MOE-modified chimeric oligonucleotide gapmer designed to hybridize to the 3'-untranslated region of VLA-4 mRNA. In one embodiment, the oligonucleotide selectively inhibits VLA-4 expression in both primary human cells and in several human cell lines by hybridizing to RNA encoding CD49, which is the α4 integrin subunit of VLA-4 and α4β7 integrin.

In one embodiment, the oligonucleotide is the 19-sodium salt of a 3'-5' phosphorothioate oligonucleotide 20mer also referred as a 3-9-8 MOE gapmer having a molecular weight of 7230 Daltons, in which the nucleotides at positions 1 to 3 from the 5' end are 2'-O-(2-methoxyethyl) (2'MOE) modified ribonucleosides (2'-O-(2-methoxyethyl ribose); the nucleotides at positions 4 to 12 from the 5' end are 2'-deoxyribonucleosides of which all cytosines are 5-methylcytosines; the nucleotides at positions 13 to 20 from the 5' end are 2'-O-(2-methoxyethyl) modified ribonucleosides.

In one embodiment, the sequence of the oligonucleotide is (SEQ ID NO:1):

The empirical formula of the oligonucleotide is:

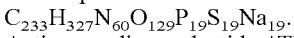

Antisense oligonucleotide ATL1102 has previously been shown to be effective in central nervous system disorder, MS and at significantly higher doses than proposed herein (Limmroth et al). The ability of antisense oligonucleotide to CD49d alpha chain of VLA-4 to selectively inhibit VLA-4 in immune cells prevents significant safety events such as PML which have characterised administration of antibodies and small molecule inhibitors of VLA-4 which are pan VLA-4 inhibitors affecting all cells which express VLA-4.

In one embodiment, all uracils are 5-methyluracils (MeU). Typically, the oligonucleotide is synthesized using 2-methoxyethyl modified thymidines not 5-methyluracils.

In one embodiment, all pyrimidines are C5 methylated (i.e., U, T, C are C5 methylated).

In one embodiment, the sequence of the oligonucleotide may be named by accepted oligonucleotide nomenclature, showing each 0-0 linked phosphorothioate internucleotide linkage:

2'-O-methoxyethyl-5-methylcytidylyl-(3'→5' O, O-phosphorothioyl)-2'-O-methoxyethyl-5-methyluridylyl-(3'→5' O, O-phosphorothioyl)-2'-O-methoxyethylguanosylyl-(3'→5' O, O-phosphorothioyl)-2'-O-deoxyadenosylyl-(3'→5' O, O-phosphorothioyl)-2'-O-deoxyguanosylyl-(3'→5' O, O-phosphorothioyl)-thymidylyl-(3'→5' O, O-phosphorothioyl)-2'-deoxy-5-methylcytidylyl-(3'→5' O, O-phosphorothioyl)-thymidylyl-(3'→5' O, O-phosphorothioyl)-2'-deoxyguanosylyl-(3'→5' O, O-phosphorothioyl)-thymidylyl-(3'→5' O, O-phosphorothioyl)-thymidylyl-(3'→5' O, O-phosphorothioyl)-thymidylyl-(3'→5' O, O-phosphorothioyl)-2'-O-methoxyethyl-5-methyluridylyl-(3'→5' O, O-phosphorothioyl)-2'-methoxyethyl-5-methylcytidylyl-(3'→5' O, O-phosphorothioyl)-2'-methoxyethyl-5-methylcytidylyl-(3'→5' O, O-phosphorothioyl)-2'-O-methoxyethyl-5-adenosylyl-(3'→5' O, O-phosphorothioyl)-2'-O-methoxyethyl-5-methyluridylyl-(3'→5' O, O-phosphorothioyl)-2'-O-methoxyethyl-5-methyluridylyl-(3'→5' O, O-phosphorothioyl)-2'-O-methoxyethyl-5-methylcytosine, (3'→5' O, O-phosphorothioyl)-2'-O-methoxyethyl-5-methyluridylyl-19 sodium salt.

The oligonucleotide may be synthesized by a multi-step process that may be divided into two distinct operations: solid-phase synthesis and downstream processing. In the first operation, the nucleotide sequence of the oligonucleotide is assembled through a computer-controlled solid-phase synthesizer. Subsequent downstream processing includes deprotection steps, preparative reversed-phase chromatographic purification, isolation and drying to yield the oligonucleotide drug substance. The chemical synthesis of the oligonucelotide utilizes phosphoramidite coupling chemistry followed by oxidative sulfurization and involves sequential coupling of activated monomers to an elongating oligomer, the 3'-terminus of which is covalently attached to the solid support.

Detritylation (Reaction a)

Each cycle of the solid-phase synthesis commences with removal of the acid-labile 5'-O-4,4'-dimethoxytrityl (DMT) protecting group of the 5' terminal nucleoside of the support bound oligonucleotide. This is accomplished by treatment with an acid solution (for example dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for base2: MOE-MeC amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding [O, O, O)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ("DMT-on (n-l)-mers") which are difficult to separate from the desired product. To prevent formation of these impurities and to facilitate purification, a "capping reagent" (e.g., acetic anhydride and N-methylimidazole/acetonitrile/pyridine) is introduced into the reactor vessel to give capped sequences. The resulting failure sequences ("DMT-off shortmers") are separated from the desired product by reversed phase HPLC purification. After the capping reaction, excess reagent is removed from the support by washing with acetonitrile in preparation of the next reaction.

Reiteration of this basic four-step cycle using the appropriate protected nucleoside phosphoramidite allows assembly of the entire protected oligonucleotide sequence.

Backbone Deprotection (Reaction e)

Following completion of the assembly portion of the process the cyanoethyl groups protecting the (O, O, O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed phase HPLC. The reversed phase HPLC step removes DMT-off failure sequences. The elution profile is monitored by UV absorption spectroscopy. Fractions containing DMT-on oligonucleotide product are collected and analyzed.

Acidic Deprotection (Reaction g)

Reversed phase HPLC fractions containing 5'-O-DMT-protected oligonucleotide are pooled and transferred to a precipitation tank. The products obtained from the purification of several syntheses are combined at this stage of the process. Purified DMT-on oligonucleotide is treated with acid (e.g., acetic acid) to remove the DMT group attached to the 5' terminus. After acid exposure for the prescribed time and neutralization, the oligonucleotide drug substance is isolated and dried.

Following the final acidic deprotection step, the solution is neutralized by addition of aqueous sodium hydroxide and the oligonucleotide drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to $-50°$ C. Primary drying is carried out at $25°$ C. for 37 hours. The temperature is increased to $30°$ C. and a secondary drying step performed for 5.5 hours. Following completion of the lyophilization process, the drug substance is transferred to high density polyethylene bottles and stored at $-200°$ C.

Suitable further antisense compounds targeting CD49d/VLA-4 are described in U.S. Pat. No. 6,258,790 assigned to Isis pharmaceuticals, Inc. and US2009/0029931 assigned to Antisense Therapeutics Ltd incorporated herein by reference in their entirety. Further antisense oligomers that target ITGA4 gene transcripts to modify pre-mRNA splicing in the ITGA4 genes are disclosed for example in International application no PCT/AU2016/000158 for Murdoch University incorporated herein by reference in its entirety.

Target Nucleic Acid

"Targeting" an antisense compound to a particular nucleic acid can be a multistep process. The process usually begins with the identification of a target nucleic acid whose function is to be modulated. In the present disclosure, the target nucleic acid encodes the alpha4 integrin chain of VLA-4 or α4β7 integrin.

The targeting process usually also includes determination of at least one target region, segment, or site within the target nucleic acid for the antisense interaction to occur such that the desired effect, for example, inhibition of expression, will result. The term "region" as used herein is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein, means positions within the target nucleic acid.

Since the "translation initiation codon" is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG, or 5'-CUG, and 5'-AUA, 5'-ACG and 5'-CUG have been shown to function in vivo. Thus, the terms "translation initiation codon" and "start codon" can encompass many codon sequences even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. The terms "start codon" and "translation initiation codon" as used herein refer to the codon or codons that are used in vivo to initiate translation of an mRNA transcribed from a gene encoding, for example, α4 integrin chain of VLA-4 or α4β7 integrin, regardless of the sequence(s) of such codons.

A "translation termination codon" also referred to a "stop codon" may have one of three RNA sequences: 5'-UAA, 5'-UAG and 5'-UGA (5'-TAA, 5'-TAG and 5'-TGA, respectively in the corresponding DNA molecule). The terms "translation termination codon" and "stop codon" as used herein refer to the codon or codons that are used in vivo to terminate translation of an mRNA transcribed from a gene encoding the α4 integrin chain of VLA-4 or α4β7 integrin, regardless of the sequence(s) of such codons.

The terms "start codon region" and "translation initiation codon region" refer to a portion of the mRNA or gene that encompasses from about 25 to about 50 contiguous nucleotides in either direction (i.e., 5' or 3') from the translation initiation codon. Similarly, the terms and "stop codon region" and "translation termination codon region" refer to a portion of the mRNA or gene that encompasses from about 25 to about 50 contiguous nucleotides in either direction (i.e., 5' or 3') from the translation termination codon. Consequently, the "start codon region" or "translation initiation codon region" and the "stop codon region" or "translation termination codon region" are all regions which may be targeted effectively with the antisense compounds of the present disclosure.

The "open reading frame" (ORF) or "coding region", which is known in the art to refer to the region between the translation initiation codon and the translation termination codon, is also a region which may be targeted effectively. In one embodiment, the intragenic region encompassing the translation initiation or termination codon of the ORF of a gene is targeted.

Other target regions include the 5' untranslated region (5'UTR), known in the art to refer to the portion of the mRNA in the 5' direction from the translation initiation codon, and thus including nucleotides between the 5' cap site and the translation initiation codon of the mRNA (or corresponding nucleotides on the gene), and the 3' untranslated region (3'UTR), known in the art to refer to the portion of the mRNA in the 3' direction from the translation termination codon, and thus including nucleotides between the translation termination codon and 3' end of the mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA transcripts produced via the process of splicing of two (or more) mRNAs from different gene sources are known as "fusion transcripts". In one embodiment, introns, or splice sites, that is, intron-exon junctions or exon-intron junctions, or aberrant fusion junctions due to rearrangements or deletions are targeted. Alternative RNA transcripts can be produced from the same genomic region of DNA. These alternative transcripts are generally known as "variants".

"Pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription, that is through use of an alternative start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the pre-mRNA or mRNA variants are targeted.

The location on the target nucleic acid to which the antisense compound hybridizes is referred to as the "target segment". As used herein the term "target segment" is defined as at least an 8-nucleobase portion of a target region to which an antisense compound is targeted. While not wishing to be bound by theory, it is presently believed that these target segments represent portions of the target nucleic acid which are accessible for hybridization.

Once one or more target regions, segments or sites have been identified, antisense compounds are chosen which are sufficiently complementary to a target segment, that is, antisense compounds that hybridize sufficiently well and with sufficient specificity, to give the desired effect.

The target segment may also be combined with its respective complementary antisense compound to form stabilized double-stranded (duplexed) oligonucleotides. Such double stranded oligonucleotide moieties have been shown in the art to modulate target expression and regulate translation, as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Compositions

Compounds of the disclosure may be admixed, encapsulated, conjugated or otherwise associated with other molecules, molecule structures or mixtures of compounds, resulting in, for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921, 5,354,844, 5,416,016, 5,459,127, 5,521,291, 5,543,158, 5,547,932, U.S. Pat. Nos. 5,583,020, 5,591,721, 4,426,330, 4,534,899, 5,013,556, 5,108,921, 5,213,804, 5,227,170, 5,264,221, 5,356,633, 5,395,619, 5,416,016, 5,417,978, 5,462,854, 5,469,854, 5,512,295, 5,527,528, 5,534,259, 5,543,152, 5,556,948, 5,580,575, and 5,595,756.

Compounds of the disclosure may be administered in a pharmaceutically acceptable carrier. The term "pharmaceutically acceptable carrier" refers to molecular entities that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbents, dispersion media, coatings, stabilizers, protective colloids, adhesives, thickeners, thixotropic agents, penetration agents, sequestering agents, isotonic and absorption delaying agents that do not affect the activity of the active agents of the disclosure.

In one embodiment, the pharmaceutical carrier is water for injection (WFI) and the pharmaceutical composition is adjusted to pH 7.4, 7.2-7.6.

In one embodiment, the salt is a sodium or potassium salt.

The oligonucleotides may contain chiral (asymmetric) centers or the molecule as a whole may be chiral. The individual stereoisomers (enantiomers and diastereoisomers) and mixtures of these are within the scope of the present disclosure.

Compounds of the disclosure may be pharmaceutically acceptable salts, esters, or salts of the esters, stereoisomers, or any other compounds which, upon administration are capable of providing (directly or indirectly) the biologically active metabolite.

The term "pharmaceutically acceptable salts" as used herein refers to physiologically and pharmaceutically acceptable salts of the compounds that retain the desired biological activities of the parent compounds and do not impart undesired toxicological effects upon administration. Examples of pharmaceutically acceptable salts and their uses are further described in U.S. Pat. No. 6,287,860.

Oligonucleotide compounds of the disclosure may be prodrugs, stereoisomers, or pharmaceutically acceptable salts of the prodrugs, or other bioequivalents. The term "prodrugs" as used herein refers to therapeutic agents that are prepared in an inactive form that is converted to an active form (i.e., drug) upon administration by the action of endogenous enzymes or other chemicals and/or conditions. In particular, prodrug forms of the antisense compounds of the disclosure are prepared as SATE [(S acetyl-2-thioethyl) phosphate] derivatives according to the methods disclosed in WO 93/24510, WO 94/26764 and U.S. Pat. No. 5,770,713.

A prodrug may, for example, be converted within the body, e. g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference. Those skilled in the art of organic chemistry will appreciate that many organic compounds can form complexes with solvents in which they are reacted or from which they are precipitated or crystallized. These complexes are known as "solvates". For example, a complex with water is known as a "hydrate".

Conventional Therapy

Corticosteroid therapy is the mainstay of DMD treatment in ambulatory patients. "Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including prednisone a precursor to prednisolone, methylprednisolone), dexamethasone triamcinolone, budesonide, and betamethasone.

In one embodiment, the treatment of the present invention for MD in a human subject with MD comprises administering to the subject an effective amount of a therapeutic agent, such as the antisense oligonucleotide to CD49d (alpha chain of VLA-4), and further comprising administering to the subject an effective amount of a second medicament, that is a corticosteroid. In one embodiment the corticosteroid is prednisone (or a prednisone equivalent), deflazacort (a derivative or prednisolone). Other corticosteroids are known in the art as mentioned above.

Combined administration herein includes co-administration, using separate formulations (or a single pharmaceutical formulation), and consecutive administration in either order, wherein generally there is a time period while both (or all) active agents simultaneously exert their biological activities.

Corticosteroid treatment at standard doses is used in DMD patients while they are ambulatory as it has been shown to have some effect in maintaining ambulation in some patients. Prolonged treatment at standard doses (0.75 mg/kg/day prednisone or 0.9 mg/kg/day deflazacort) however can result in muscle atrophy and/or has other side effects. There is no standard of care in non-ambulatory DMD patients who may stay on CS, sometimes at the fixed dose of CS they were on when they lost ambulation, which is a reduced mg/kg/day dose of CS, or they may come off CS treatment because of the side effects and/or absence of benefit. As proposed and shown herein antisense treatment to CD49d in conjunction with corticosteroid treatment, including reduced levels of corticosteroid treatment, in non-ambulatory subjects reduced or delayed progression of muscle function. It is unclear if the CS treatment was providing any benefit in such subject, so this supports ATL1102 monotherapy or treatment of combinations.

As used herein, the term "combination" in the context of the administration of a therapy refers to the use of more than one therapy or therapeutic agent. The use of the term "in combination" does not restrict the order in which the therapies or therapeutic agents are administered to a subject. A therapy or therapeutic agent can be administered prior to, concomitantly with, or subsequent to the administration of a second therapy or therapeutic agent to a subject.

Administration

In one embodiment, the antisense compound of the disclosure is administered systemically. As used herein "systemic administration" is a route of administration that is either enteral or parenteral.

As used herein "enteral" refers to a form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense compound in suppository or enema form.

As used herein "parenteral" includes administration by injection or infusion. Examples include, intravenous (into a vein), intraarterial (into an artery), intramuscular (into a muscle), intracardiac (into the heart), subcutaneous (under the skin), intraosseous infusion (into the bone marrow), intradermal, (into the skin itself), intrathecal (into the spinal canal), intraperitoneal (infusion or injection into the peritoneum), intravesical (infusion into the urinary bladder) transdermal (diffusion through the intact skin), transmucosal (diffusion through a mucous membrane), inhalational.

In one embodiment, administration of the pharmaceutical composition is subcutaneous.

The antisense compound may be administered as single dose or as repeated doses on a period basis, for example, daily, once every two days, three, four, five, six seven, eight, nine, ten, eleven, twelve, thirteen or fourteen days, once weekly, twice weekly, three times weekly, or every two weeks, or every three weeks.

In one embodiment, administration is 1 to 3 times per week, or once every week, two weeks, three weeks, four weeks, or once every two months.

In one embodiment, administration is once weekly.

In one embodiment, a low dose administered for 3 to 6 months, such as about 25-50 mg/week for at least three to six months and then up to 12 months and chronically.

Illustrative doses are between about 10 to 300 mg. Illustrative doses include 25, 50, 100, 150, 200 mg. Illustrative doses include 0.1 mg/kg, 0.4 mg/kg, 0.5 mg/kg, 1 mg/kg 1.5 mg/kg (about 50 to 100 mg) and 3 mg/kg (100-200 mg) and 4.5 mg/kg (150-300 mg). In one embodiment doses are administered once per week. Thus in one embodiment, a low dose of approximately 10 to 30, or 20 to 40, or 20 to 28 mg may be administered to subjects typically weighing between about 25 and 65 kg. In one embodiment, the antisense oligonucleotide is administered at a dose of less than 50 mg, or less than 30 mg, or about 25 mg per dose to produce a therapeutic effect. In one embodiment the antisense oligonucleotide, ATL1102 is administered at a dose of less than 50 mg, or less than 30 mg, or about 25 mg per dose to produce a therapeutic effect.

In one embodiment, a therapeutic effect such as a delay in progression is seen within about three months after administration of the first dose. The term "therapeutically effective amount" as used herein refers to a dose of the antisense compound sufficient for example to improve one or more markers, signs or symptoms of muscular dystrophy or to delay progression of muscular dystrophy in a subject, or to improve one or more markers, signs or symptoms of dystrophic myofibres or to delay progression of muscular dystrophy in a subject under the conditions of administration.

In another embodiment, the administration is effective to provide a Cmax of the oligonucleotide in the plasma of the human subject upwards of 2890 ng/mL and in one embodiment, about 10,000-11,000 ng/mL.

In another embodiment, the administration is effective to provide a Cmin or Ctrough of the oligonucleotide in the plasma of the human subject of at least 2.5 ng/mL, in one embodiment at least 20 ng/mL, or at least 45 ng/mL.

Studies are conducted to demonstrate the treatment of muscular dystrophy with an inhibitory oligonucleotide to VLA-4 integrin which reduces the level of VLA-4 in the blood or muscle of human subjects. Reduction in the level of VLA-4 may be detected in subsets of cells in one or more organ including blood, muscle or lung. In one embodiment, subjects are taken off corticosteroids approximately 24 hours prior to administration.

This allows an assessment of the effects of inhibitory antisense oligonucleotide to the CD49d alpha chain of VLA-4 integrin in immune cells in the absence of corticosteroid, which is not present in significant levels in the blood stream at 24 hours after administration to be having an effect on circulating immune cells.

Example 1

In one embodiment, ATL1102 is administered to non-ambulant juvenile (or pubescent) boys 10 years or older with DMD weekly at about 1.5 mg/kg (about 50 to 100 mg) and 3 mg/kg (100-200 mg) and 4.5 mg/kg (150-300 mg) for up to 12 weeks. The effects of the administered oligonucleotide for example on motor/muscle function and inflammatory markers are measured. Markers for muscle degeneration-regeneration and fibrosis are also assessed. Markers may be detected in situ or samples such as in plasma, urine, or muscle biopsy. Inspiratory and expiratory pressures, peak cough flow, FVC are assessed to evaluate change in respiratory performance. Percent change in normalized upper extremity reachable surface area, percent change in Performance of the Upper Limb Assessment score, percent change in Person-Reported Outcome Measure Upper Limb (PROM-UL) functional capacity score are used to assess muscle function. Quality of life questionnaires are useful in determining the effect of treatments.

Corticosteroid may be dosed daily, or less frequently. Prednisolone may be dosed at 0.75 mg/kg/day and Deflazacort 0.9 mg/kg/day as standard therapies for ambulant DMD patients, at two thirds standard doses, half the dose, or a third the dose.

Example 2

In one embodiment, ATL1102 is administered to ambulant paediatric boys 4-11 years old with DMD weekly at about 1.5 mg/kg (about 10 to 100 mg) and 3 mg/kg (20-200 mg) and 4.5 mg/kg (30-300 mg) for up to 12 weeks. The effects of the administered oligonucleotide for example on motor/muscle function and inflammatory markers are determined. Ambulant paediatric boys may be good walkers or poor walkers. Maintenance or reducing the loss of walking capacity may be assessed by the methods known to those skilled in the art.

Example 3

In one embodiment, 10 non-ambulant DMD patients 12 to 18 years of age receive ATL1102 at a starting dose of 3 mg/kg once weekly for 4 weeks. The first 5 patients continue dosing at 3 mg/kg/week for a further 4 weeks and the remaining 5 patients dose escalate to 4.5 mg/kg/week (twice weekly 2.25 mg/kg) for 4 weeks. After 8 weeks of treatment a 4 week monitoring period is performed. In the treatment and monitoring period, assessments are at baseline, 2 weeks, 4 weeks, 6 weeks, 8 weeks, and 10 and 12 weeks. The primary activity outcome is to assess the number of circulating lymphocytes, CD4+ and CD8+ T cells, and hi CD49d T cells at 4 and 8 weeks of treatment vs baseline and safety including injection sites reactions, platelet changes, liver enzyme GGT-bilirubin, CRP and albumin, A/G ratio changes. Secondary endpoints clinical assessments are measures of strength, in upper limb function, and functional capacity, quality of life, and respiratory markers and MRI assessment of muscle fibrosis, fat inflammation-oedema and atrophy and pharmacokinetics. Exploratory outcome measures will include serum/plasma biomarker response such as those related to muscle inflammation muscle fibrosis, muscle apoptosis/degeneration, and muscle regeneration including cytokines, and proteomics and mononuclear cell RNA array and exosome RNA.

Example 4

Low-Dose Administration of Inhibitory Oligonucleotide

In one embodiment, 9 non-ambulant DMD patients 10 to 18 years of age, 25 to 65 kg in weight receive ATL1102 at a starting dose of 25 mg once weekly for 24 weeks. After 24 weeks of treatment an 8 week monitoring period is performed. In the treatment and monitoring period, assessments are at baseline, and every 2 weeks during the treatment period, and every 4 weeks in the post-treatment monitoring period. The primary activity outcome is to assess the number of circulating lymphocytes, CD4+ and CD8+ T cells, and hi CD49d T cells at 4 and 8 weeks of treatment vs baseline and safety including injection sites reactions, platelet changes, liver enzyme GGT-bilirubin, CRP and albumin, A/G ratio changes. Secondary endpoints for clinical assessments are measures of muscle strength, and upper limb function, strength as measured by myoset, and limb functional capacity as measured by PUL-2 (performance of upper limb module for DMD 2.0), quality of life, and respiratory markers and MRI assessment of muscle fibrosis, fat inflammation-oedema and atrophy and pharmacokinetics. Exploratory outcome measures will include serum/plasma biomarker response such as those related to muscle inflammation muscle fibrosis, muscle apoptosis/degeneration, and muscle regeneration including cytokines one or more of which may be markers of muscle injury, and proteomics and mononuclear cell RNA array and potentially exosome RNA.

Example 5

Results of Patient 1 at 12 Weeks

A low dose of 25 mg/week of ATL1102 was administered for 12 weeks to a 13 yr old non-ambulent subject of 62 kg weight, on a 30 mg daily dose of corticosteroid (CS) Deflazacort (0.48 mg/kg/day). ATL1102 was effective in reducing the number of cells per microlitre of circulating CD8+ cells and CD8+ cells expressing high levels of CD49d observed in this patient at baseline (week 1) prior to his daily dose of CS, reducing markers of muscle injury as measured by biochemistry exploratory markers, muscle strength as measured by myoset, and importantly muscle function as measured by PUL-2.0. This subject had lost ambulation approximately 2.5 years ago and was on 54% (~50%) of the standard of care 0.90 mg/kg/day dose of Deflazacort use to treat subjects with DMD when ambulant. The equivalent prednisolone dose used as standard of care is 0.75 mg/kg/day in DMD when ambulant.

Immune Cells

The ATL1102 effects on immune cells were measured by flow cytometry and hematology at baseline (week 1), week 5 (3 days past the ATL1102 dose), and weeks 8 and 12 (7 days past the week 8 and week 12 doses). The ATL1102 effects on CD8+ cells was relatively selective compare to prior experiences at higher ATL1102 doses used in multiple sclerosis (MS) (Limmroth et al 2014). The effects were also more prolonged than 3 days post dosing as previously measured in the MS study, with effects shown for the first time 7 days post ATL1102 dosing. Certain immune cells were not affected at this dose and time of assessment indicated the ATL1102 effect are relatively more specific at this low 25 mg dose, of 0.4 mg/kg/week. For instance there were no significant reductions on neutrophils or platelets as observed at higher doses with ATL1102 in the MS study (Limmroth et al).

Myoset—Muscle Strength Data

Myoset preliminary data from this subject 1 suggests after 12 weeks of dosing compared to baseline he has had loss of strength in the dominant hand as measured by myogrip, but no loss of strength in the thumb as measured by myopinch, nor loss in finger strength as determined by moviplate with the number of taps being the same after 12 weeks versus baseline. The data in the other hand suggests no loss of strength in the hand, or fingers and a numerically more strength in the thumb at week 12 compared to baseline. Ricotti et al (2016) looked at 15 patients (14 treated with CS) treated for 12 weeks and longer with CS and myoset and observed a mean trend reduction of 0.22 kg in the myogrip, and reduction of 0.1 kg in the myopinch compared to baseline, and increase in moviplate.

PUL-2-Function Data

PUL-2 for DMD is an updated version of PUL-1 used to measure upper limb function. PUL-2 measures higher level shoulder function with a maximum score out of 12, mid level elbow function with a maximum score of 17, and distal wrist and hand function with a maximum score of 13. An entry score of 3 to 6 means (6 being the highest, and zero the lowest) indicates a subject can be assessed for shoulder function.

Subject one had an entry level function score of 5, and measurements recorded indicates he has had over 12 weeks of dosing, no loss in the function in the shoulder with a score of 8 at baseline and week 12. Subject 1 gained function in the mid-level elbow with a score of 14 at week 12 vs 13 at baseline, and has gained function in the distal wrist and hand dimension with a score of 12 at week 12 vs 10 at baseline. At 12 weeks of dosing compared to baseline, the PUL-2.0 total function score was 34 compared to 31. The patient entry level score also increased from level 5 at baseline to level 6 consistent with the PUL-2 results recorded.

ATL1102 add on therapy may help retain muscle strength as measured by myoset, and appears to maintain function as measured by PUL-2 if not improve function in this subject. ATL1102 therapy may thus slow progression of disease.

Results validate the use of antisense to CD49d (alpha chain of VLA-4) generally and ATL1102 specifically to treat DMD patients, to improve and stabilize muscle strength and limb function and slow progression of muscle dystrophy disease as a monotherapy or in combination with CS.

As the skilled person will appreciate, the key elements of muscle performance are strength which is the greatest force and which is conveniently measured by in myogrip and myopinch tests. Also, endurance/fatigability, which is the ability to sustain forces repeatedly e.g tested for example with repeat measurements of myogrip and myopinch. Also, power which is force/unit time like a six minute walk test. Motor performance is the movement of action of muscle such as gross motor skills and fine motor skills in wrist hands fingers, feet and toes. It would be understood by the skilled artisan, that motor performance includes every day life activities related to the upper limb, or lower limbs, or in animals front and hind limbs. In non-ambulant children with DMD modules are available to measure such upper limb performance like PUL 1.0, PUL1.2, PUL2.0, and these can also be used for ambulant children with DMD and other conditions.

It would further be understood by those skilled in the art that muscle strength may be a measure of upper limb or lower limb strength, and in the upper limb muscle strength is used for shoulder flexion, elbow extension, and wrist extension as measured in grams, or pounds, using a hand held myometer.

The myoset measures strength and fatigability of the upper limb, as there are repeated measures, (data for fatigability is not shown), as we mostly provide the strength maximum result of three or more repeated valid results. Sometimes the largest result is the second or third test.

Exploratory Pharmacodynamic Outcome Measures of Muscle Injury

Creatine kinase (CK), Aspartate aminotransferase (AST), and Lactate dehydrogenase (LDH) are measures of muscle injury in boys with DMD primarily related to low levels of dystrophin or no dystrophin and injury to muscle upon contraction, and secondarily related to inflammatory and other downstream damage to muscle. Creatine kinase (CK), Aspartate aminotransferase (AST), and Lactate dehydrogenase (LDH) are measures of muscle injury in young ambulant patients with DMD, who have more muscle mass and inflammation than non-ambulant patients.

Blood and serum samples were nevertheless collected to investigate muscle injury marker changes in subject 1. In subject 1 CK, ALT, AST, LDH were reduced at week 8 and 12 compared to baseline and week 5. The baseline/week 5 levels in units/litre for CK, ALT, AST, LDH respectively were in 5860/6881, 304/404, untested/184, and 632/681 compared to week 8/12 levels of 4606/5358, 265/250, 116/134, and 564/498. The LDH levels were reduced from what is considered high to within the normal range. This suggests signs of muscular injury, related to dystrophin loss or inflammation or other damage has been reduced in this non-ambulant patient.

Example 6

Results of 4 Patient Twelve Week Data and 2 Patient 24 Week Data

Data from 4 non ambulant patients, including patient 1, over 12 weeks, is consistent with the example 5 observations in patient 1, and supports 25 mg once weekly treatment of ATL1102 improving and maintaining muscle strength and limb function. The 4 patients had lost ambulation over a range of 9 months to 4.5 years, at between 10 to 15 years of age, and were 13 to 17 years of age when initiating ATL1102 treatment. With a weight ranging from approximately 40 to 65 kg of weight they were receiving approximately 0.4 to 0.6 mg/kg/week of ATL1102. They had all been taken off standard of care 0.90 mg/kg/day dose of Deflazacort and 0.75 mg/kg/day of Prednisolone use to treat subjects with DMD when ambulant, and were on fixed 20 and 25 mg doses of Prednisolone and 30 mg doses of Deflazacort, which is approximately half, two fifths, and four fifths the standard dose of these steroids when use in ambulant patients.

Data from 2 non ambulant patients, including patient 1, over 24 weeks, is also consistent with observations over 12 weeks. The 2 patients had lost ambulation at 2.5 years to 4.5 years respectively, at 10 to 13 years of age, and were 13 and 17 years of age when ATL1102 treatment was initiated. With a weight of approximately 60 to 65 kg they were receiving approximately 0.4 mg/kg/week of ATL1102. Patient 1 was on 30 mg deflazacort and patient 2 on 20 mg prednisolone, which is 54% and 40% respectively the standard daily dose of CS used in ambulant patients.

Myoset: Myogrip and Myopinchmuscle Strength Data

Myogrip and myopinch data is generated with the dominant arm and the non-dominant arm, and grip and pinch test done several times at each time point. This allows one to obtain valid results and to determine the muscle strength and endurance.

Myogrip—Muscle Strength Data

Myogrip data from the 4 DMD patients after 12 weeks of dosing compared to baseline was assessed in the dominant arm used by the patient as recommended by the myoset suppliers. The myogrip strength in the dominant hand showed a mean gain of 0.09 kg and a 10.52% gain of strength from baseline. Ricotti et al (2016) looked at 15 patients (14 treated with CS) treated for 12 weeks and observed in the 10 patients analysed for myogrip at 12 weeks a trend mean loss of 0.22 kg and a 3.28% loss of myogrip strength compared to baseline.

Myogrip data from the 2 DMD patients after 24 weeks of dosing compared to baseline was assessed in the dominant arm used by the patient. The myogrip strength in the dominant hand showed a mean loss of only 0.42 kg and a mean 1.24% loss of strength from baseline. Ricotti et al (2016) in the 9 patients analysed for strength at 24 weeks showed a significant mean loss of 0.50 kg and 10.45% loss of myogrip strength compared to baseline.

Myopinch—Muscle Strength Data

Myopinch data from the 4 DMD patients after 12 weeks of dosing compared to baseline was assessed in the dominant arm used by the patient as recommended by the myoset suppliers. The myopinch strength in the dominant hand showed a mean gain of 0.169 kg and a 5.31% gain of strength from baseline. Ricotti et al (2016) observed in the 10 patients analysed for myopinch at 12 weeks a mean trend loss of 0.1 kg in the and 4% loss of myopinch strength compared to baseline.

Myopinch data from the 2 DMD patients after 24 weeks of dosing compared to baseline was assessed in the dominant used arm used by the patient. The myopinch strength in the dominant hand, showed a mean gain of 0.034 kg and a minus 2.58% loss of strength from baseline. Ricotti et al (2016) in the 9 patients analysed for myopinch at 24 weeks showed a significant mean loss of 0.38 kg and 15.2% loss in the myopinch compared to baseline.

Moviplate

Moviplate data from the 4 DMD patients after 12 weeks of dosing compared to baseline was assessed in the dominant arm used by the patient as recommended by the myoset suppliers. The moviplate in the dominant hand showed a mean tap rate in 30 seconds of 63.5, with an increase in the mean number of taps by 4 versus baseline. Ricotti et al (2016) observed in the 10 patients analysed for Moviplate at 12 weeks a mean increase of 2.3 taps compared to baseline.

PUL 2 Limb Muscle Function Data

PUL 2.0 data from the 4 DMD patients after 12 weeks of dosing compared to baseline was assessed. The PUL 2.0 total function score showed a mean gain of 3.66 points, and a mean gain of 9.6% from baseline. Three patients had a gain of +3 points, and one patient a gain of +2 points from baseline.

PUL 2.0 data from the 2 DMD patients after 24 weeks of dosing compared to baseline was assessed. The PUL 2.0 total function score showed mean gain of 2 points, and a gain of 9.9% from baseline. Both patients had a gain of +2 in the total function score.

Pane et al (2018) observed in 90 non-ambulant patients with DMD, the PUL 2.0 function data at baseline, 12 months and 24 months. Fifty two of 90 patients, i.e 58%, were on CS. Results were linear over this 24 period and showed significant loss over a 12 and 24 month time period. Extrapolations suggest an estimated mean total function score loss of 1, and an estimated mean loss of 5.4% in the PUL 2.0 total function score compared to baseline.

Subject one had an entry level baseline function score of 5 out of a possible 6, that increased to level 6 at 12 weeks and remained at levels 6 at 24 weeks. Patient 2 had an entry level baseline function score of 1, just above the lowest possible score of zero, and the entry score increased to level 2 at 12 weeks and remained at level 2 at 24 weeks. The other patients remained at the baseline entry levels of 3. An entry score of 3 to 6 means (6 being the highest, and zero the lowest) indicates a subject can be assessed for shoulder function.

PUL-2 measures higher level shoulder function with a maximum score out of 12, mid level elbow function with a maximum score of 17, and distal wrist and hand function with a maximum score of 13. At 12 weeks, patients 1,2,3, and 4, had a score difference of zero, zero, +2 and +3 vs baseline and at week 24, of zero and zero. The function in the mid-level elbow at week 12 vs baseline, was +1, _2, +1, and −1 respectively, with a +1 and +2 at week 24. The function in the distal wrist and hand dimension at week 12 vs baseline was +2, zero, zero, and +1, and at 24 weeks +1 and +0.

Results validate the use of antisense to CD49d (alpha chain of VLA-4) generally and ATL1102 specifically to treat DMD patients, to improve and stabilize muscle strength and limb function and slow progression of muscle dystrophy disease as a monotherapy or in combination with CS.

Example 7

Antisense Oligonucleotide to CD49d MDX Mouse Study

ATL1102, the antisense inhibitor to human CD49d has been investigated as described herein as a treatment to reduce inflammatory, immune mediated muscle fibre damage in DMD patients. ATL1102 effects on muscle strength and muscle function are outlined in examples 5, 6 and 7 and are the first to show the effects of any inhibitor to CD49d, or VLA-4 in the treatment of DMD. Currently corticosteroids (CS) are used to reduce the inflammation observed in DMD, and CS were used in the above human study in patients 1, 2, 3 and 4. However, corticosteroids have a range of serious side effects when used for a prolonged period, as required in DMD, therefore, it would be preferred to use lower doses of CS, such as tested in the human study, and also to avoid the use of CS. That is not always possible in humans, so this was tested in mice.

The following animal study is the first to test the effects of an antisense inhibitor to CD49d, the alpha chain of VLA-4, as a monotherapy in a muscular dystrophy. It is also the first to test the effects of any inhibitor of CD49d or VLA-4 in muscular dystrophy. Moreover, this is the first to test any anti-inflammatory, immune mediated treatment post initiation of the muscle injury in muscular dystrophy mouse model, as other treatments have been done prophylactically during the initial phase of muscular injury.

ATL1102, the antisense inhibitor to human CD49d is not homologous to mouse CD49d RNA, so ISIS 348574, an antisense oligonucleotide inhibitor of mouse and human CD49d was used in a mouse study.

Methods—The study was a blinded study. A total of 48 C57BL10 MDX male mice were purchased from JAX and 12 wild type (WT) C57BL10 male mice. Two groups of 12 MDX mice were injected subcutaneously, (s.c) with ISIS 348574 at 20 mg/kg once weekly and 5 mg/kg once weekly. One group of 12 MDX mice were injected s.c with ISIS 358342 a scrambled mismatch control oligonucleotide at 20 mg/kg once weekly. One group of 12 WT controls mice were injected with saline s.c and used as a measure of disease development in the MDX mice. The groups were as follows:

WT-C57BL10 n=12 (placebo, control, saline s.c)
MDX n=12 (High dose ISIS 348574 20 mg/kg s.c)
MDX n=12 (Low dose ISIS 348574 5 mg/kg s.c)
MDX n=12 (High dose scrambled mismatch control ISIS 358342, 20 mg/kg s.c)
MDX n=12 (placebo control, saline s.c)

The controls for this study include a saline control for both WT, MDX as well as a scrambled oligonucleotide control at the high dose only. The scrambled mixed up nucleotide sequence that does not bind to the CD49d RNA has the same nucleotide composition as the oligonucleotide to CD49d. A high dose (20 mg/kg) and low dose (5 mg/kg) of ISIS 348574 was selected as doses in mice correspond, based on exposure levels, to approximately five times lower mg/kg doses in the clinic i.e 1 mg/kg and 4 mg/kg per week in the clinic. A 4 mg/kg per week dose is below the three and twice weekly 200 mg dose of ATL1102 in MS patients administered in the acute 8 week study (Limmroth et al, 2014). A 4 mg/kg and 1 mg/kg per week dose however, includes higher doses than those given of ATL1102 to the DMD patients in examples 5, 6 and 7 on a mg/kg per week basis, although the latter is a chronic 24 week study. Patients in the clinic can be provided antisense at these concentration with a suitable volume injected in the clinic.

ISIS 348574 (ATATTTTTCCACCTGTGCCC: SEQ ID NO: 2), a 5-10-5 MOE gapmer w/phoshorothioate backbone and 5-methylcystosine for every C that is fully complementary to mouse and rat integrin α4.

An 8 base pair-mismatch oligonucleotide for ISIS 348574 was also run. This was ISIS 358342 (ACAGTGTACCTCCTTTTCTC: SEQ ID NO: 3), a 5-10-5 MOE gapmer w/phoshorothioate backbone.

Only male mice were assessed as DMD is an X-linked inherited muscle disease that only effects boys. A total of n=12 MDX mice per treatment group were used to ensure enough animals were treated as per protocol to power up the study. The MDX mice and WT controls were acclimatized, and treatment began at 9 weeks of age (after initiation of the first round of muscle damage thought to occur between weeks 2 to 5 weeks of age). Treatment was for 6 weeks by subcutaneous injections with either saline, scrambled oligonucleotide or two doses of antisense to CD49d (20 mg/kg (high) and 5 mg/kg (low)) once weekly.

Mice were tested for grip strength, and by in situ muscle physiology looking at fatigue, isometric contractions (absolute and specific force), and eccentric contraction induced muscle damage. Tissues were connected to the blood and nerve supply. Skeletal muscles, diaphragm, heart, spleen and blood were collected and stored for future biochemical and molecular analyses. Reference may be made to the following publications for the techniques employed: Hogarth et al. Nature Communications 8:14143, 2017 (eccentric contractions), Garton et al. The American Journal of Human Genetics 102, 845-857, 2018 (force frequency and fatigue).

Drug Administration and Grip Strength Testing

Prior to the first injection mice underwent a baseline grip strength test to examine forelimb strength. Once completed all mice were injected with a maximum volume of 150 microliters once per week for 6 weeks using the above concentrations of antisense oligonucleotide to CD49d, saline or scrambled oligonucleotide. Mice then underwent grip strength assessments as outlined below every second week (total of 4 tests) until the completion of the 6 week treatment period.

The PROCEDURE for Grip strength was as follows:
1. Weigh the mouse.
2. Lift the mouse by the tail to the height where the front paws are at the same height as the bar.
3. Move the mouse horizontally towards the bar until it becomes within reach. Visually check that the grip is good i.e. a symmetric, right grip with both paws and exerting a detectable resistance against the investigators pull.
4. Gently pull the mouse away until its grasp is broken. Measurements must be discarded if the animal uses only one paw or also uses its hind paws, turns backwards during the pull, or leaves the bar without resistance.
5. Repeat the test 5 times with a 1 minute rest between attempts to obtain the best performance.
6. Return mice to the home cage and place sunflower seeds in the bottom as a food reward.

Tissue Collection and In Situ Muscle Physiology

The analysis of skeletal muscle function was performed using equipment developed by Arora Scientific. This technique has been used in the laboratory conducting the study for ~5 years and is the gold standard method to determine the functional effects of muscle performance and strength in many disorders associated with skeletal muscle. This system allows the determination of the strength generated by the tibialis anterior (TA, hind leg muscle) while maintaining an intact blood supply and nervous system. The effects of muscle fatigue were assessed by performing repeated muscle contractions and recovery (post fatigue) and muscle force loss was measured following eccentric contractions to assess muscle damage. Collecting this information is not possible using other methods such as in vivo grip strength, which only provides an estimate of muscle force. This method was used to assess the effect of the antisense oligonucleotide drug following 6 weeks of treatment. Analyses was staggered with a maximum of 10 mice completed per day and conducted via the following procedure PROCEDURE for Muscle Physiology was as follows:
1. Weigh mouse.
2. Anaesthetise the mouse using isoflurane. Ensure adequate initial anaesthesia using toe pinch as an indicator. Monitor the depth of anaesthesia every 5 minutes during the procedure using toe pinch.
3. After the mice have been anesthetized adequately, expose the tendon at the foot by making a ~2 mm incision in the skin.
4. Using 5-0 surgical suture tie the exposed tendon ~5 mm distal to the myotendinous junction with two separate suture leads. One anchor knot and one knot to secure to the force transducer).
5. Remove the skin from the knee and expose the patella.
6. Cut the skin over the quadriceps and expose the sciatic nerve
7. Immobilize the knee by passing a stainless steel pin or syringe needle behind the patellar tendon without damaging the surrounding tissue. The pin should affix to the base of the platform. The anesthetized animal must be secured firmly to prevent any movement during contraction.
8. Using the suture from step 4, tie the tendon of the muscle to the lever arm of the dual-mode servomotor.
9. Place two wire (simulating) electrodes on (or hooked under) the nerve and stimulate the muscle to contract using a supramaximal voltage (i.e. ~10 V) of square wave pulses of 300-400 ms duration.
10. All stimulation parameters and contractile responses are controlled and measured using appropriate computer software.
11. It is common to determine optimal muscle length (Lo) by progressively increasing the length in small increments until maximum twitch force is obtained.
12. After determination of Lo, stimulate the muscle at increasing frequencies to construct a full frequency-force relationship. The muscle should be rested for 30 seconds between success contractions. Maximum force is determined from the plateau of the frequency-force relationship.
13. Once maximum force has been determined, the muscle can be subjected to different protocols to determine power of shortening, muscle fatigue, or susceptibility to contraction induced damage.
14. At the end of the stimulation protocol collect blood via cardiac bleed and euthanise the mouse via cervical dislocation and cardiac puncture.
15. Collect the Tibialis anterior (and other muscles/tissues required for biochemical and RNA analysis) and weigh the muscle to enable specific force measurements to be calculated from the force frequency relationship.

Mice are anesthetized for the duration of the procedure and culled immediately post the procedure without recovery.

Statistical Analysis

Statistical analyses were performed using Graphpad Prism. Grip strength, absolute and specific muscle force and muscle weights obtained from 12 mice per group were assessed using One-way ANOVA, Fishers LSD test. Muscle fatigue analyses were carried out in 12 mice per group using Two-way ANOVA, Fishers, LSD test and for eccentric contractions, 9 mice per group using either One or Two-way ANOVA, LSD test.

Results

Figure 1B:
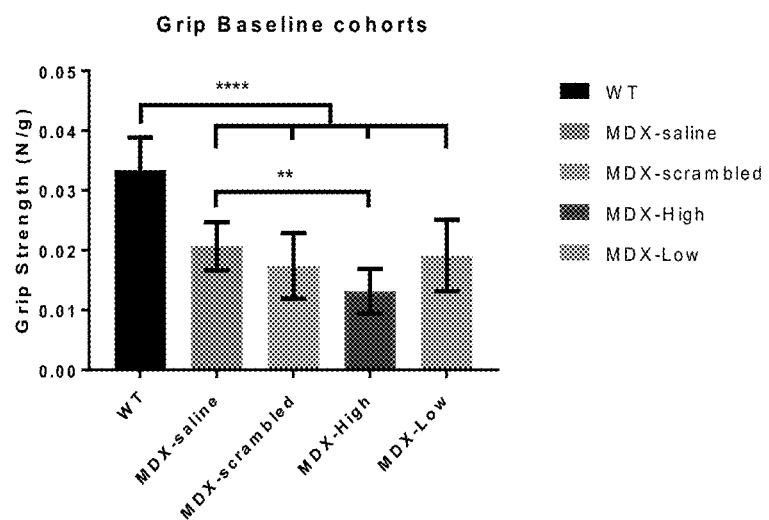

Grip Strength—The Grip strength at baseline and over the 6 weeks of treatment (mean and SEM). At baseline prior to treatment, the mdx cohorts were significantly weaker than WTs (FIG. 1A) Although the study was blinded, and animals split randomly, the MDX mice in the high dose antisense oligonucleotide cohort were significantly weaker than MDX-saline (but not MDX-scrambled or low dose) at baseline (FIG. 1B).

In Situ Tibialis Anterior (TA) Muscle Physiology

Muscle Mass and isometric muscle contraction data (max absolute force and max specific force). Table 1 provides the muscle physiology characteristics. The WT mice had a lower TA mass (mg) than the MDX mice as is known in the literature. In the four groups of MDX mice there was no difference in the muscle mass at the end of the study. There was no difference between WT, nor any of the MDX treated groups with regard to maximum absolute force as measured by mN at a twitch at less than 50 Hz. The WT mice had the largest maximum specific force (mN/mm2), and there were no significant differences between the treatment arms in the MDX mice.

Fatigue

Figure 2A:
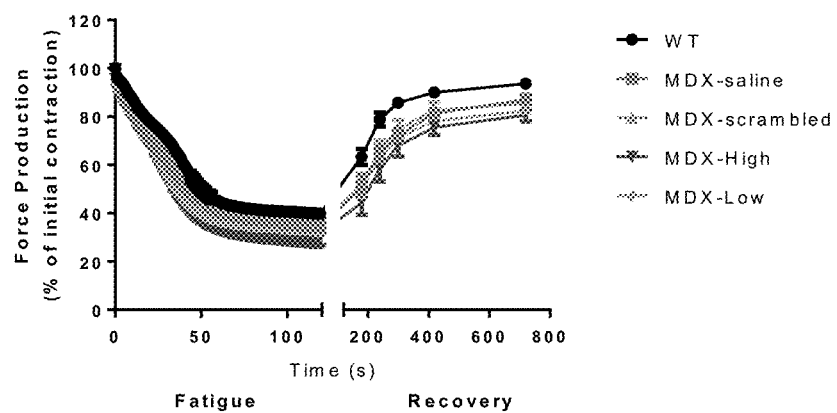
FIGS. 2A and 2B are a graphical representation of data illustrating no observed difference between MDX high dose antisense drug treatment and other MDX or control treatments in muscle fatigue recovery. Each set of four columns in FIG. 2B illustrates force production over time for, from left to right: MDX-saline; MDX-scrambled; MDX-high; and MDX-low.
Figure 2B:
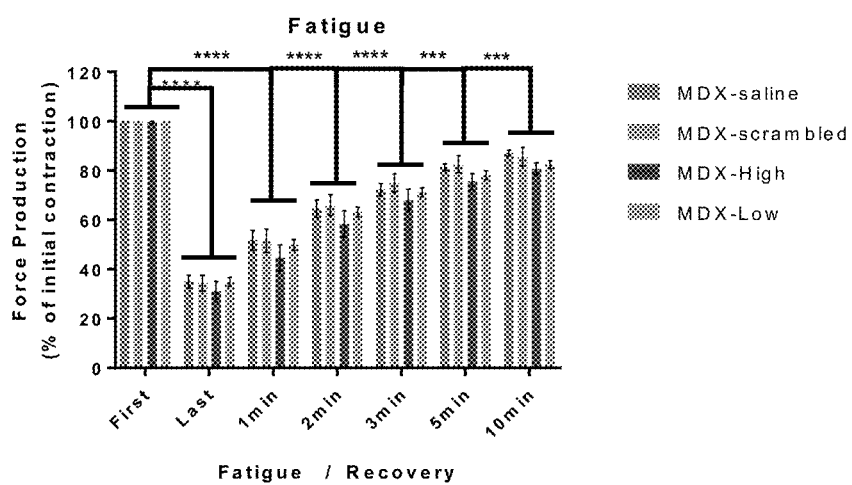

Both WT and MDX mice fatigue significantly. WT regain force within 10 min of recovery. MDX recover after 10 min but still generate less force than at baseline. There was no difference between MDX-high dose antisense drug vs other MDX (saline, scrambled control high dose or low dose antisense drug) (FIG. 2A, B).

Eccentric Muscle Contraction Data

Figure 3:
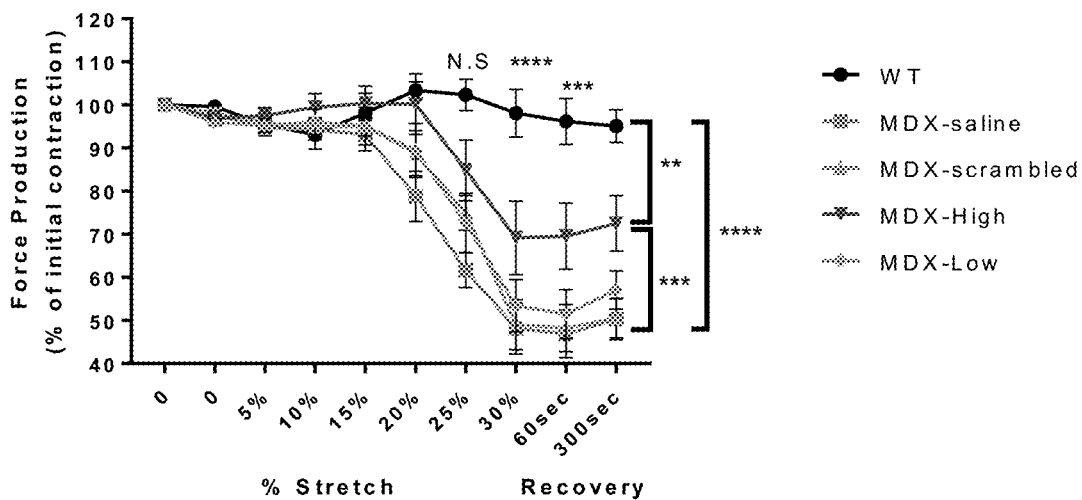
FIG. 3 is a graphical representation of data illustrating eccentric muscle contractions compared to wild type controls +/−SEM. High dose inhibitory oligonucleotide treatment delays muscle damage during eccentric contraction.

FIG. 3 shows the eccentric muscle contractions compared to wild type control. Compared to WT, all MDX cohorts show a loss of force. The high antisense oligonucleotide dose group however, showed only a significant force loss from 30% stretch (p,0.0001) whereas mdx-saline, showed a significant loss (p=0.001) at 20% stretch. This indicates the high dose antisense treatment delays muscle damage during eccentric contraction.

Figure 4:
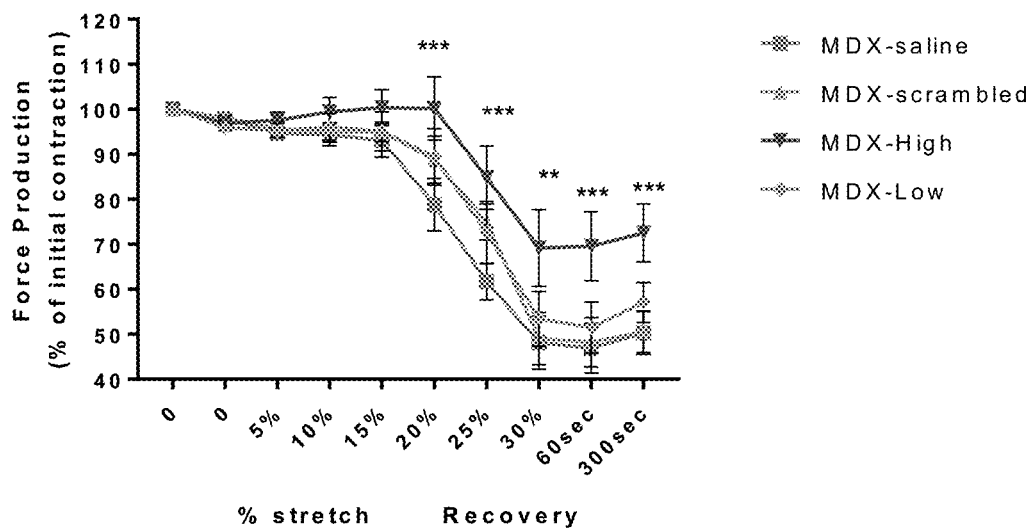
FIG. 4 is a graphical representation of data illustrating eccentric muscle contractions compared to MDX-saline treated mice. The high dose inhibitory oligonucleotide group showed significantly higher force producing capacity and drug delayed muscle damage compared to the MDX control group.

FIG. 4 shows eccentric muscle contractions compared to mdx-saline+/−SEM. Compared to MDX-saline the high dose antisense group showed a significantly higher force producing capacity from a 20% stretch (p=0.001). This suggests the antisense oligonucleotide drug delayed muscle damage and produced a greater muscle force, following eccentric contraction compared to mdx-saline treated animals.

Figure 5:
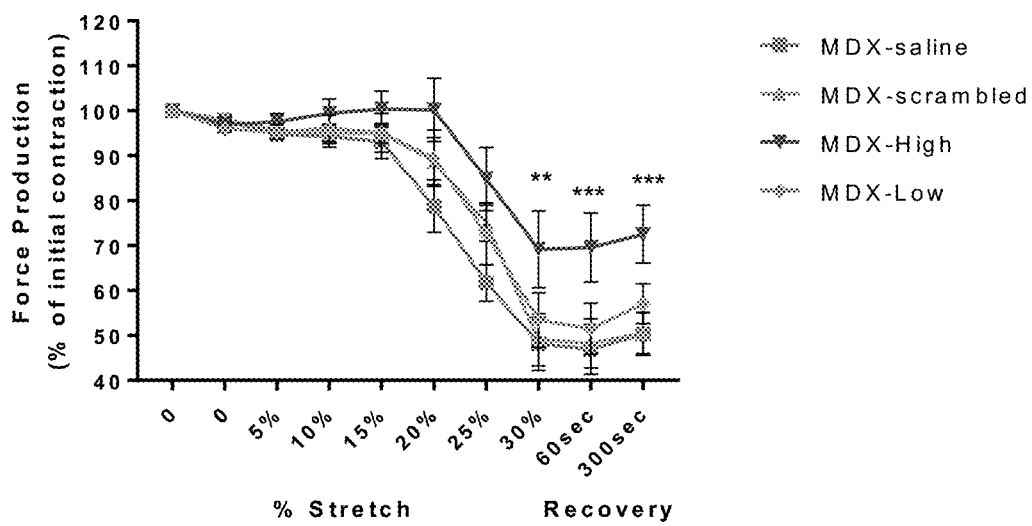
FIG. 5 is a graphical representation of data illustrating eccentric muscle contractions compared to MDX scrambled controls. High dose inhibitory oligonucleotide specifically delayed muscle damage and produced a greater muscle force following eccentric contraction compared to the scrambled negative control at the same dose.

FIG. 5 shows the eccentric muscle contractions compared to MDX-scrambled control+SEM. Compared to the scrambled oligonucleotide control the high dose antisense oligonucleotide to CD49d, shows significant increased force production from a 30% stretch (p=0.01). This suggests the antisense drug to CD49d specifically delayed muscle damage, and produced a greater muscle force, following eccentric contraction compared to the scrambled oligonucleotide control at the same dose in treated animals.

After 5 minutes of recovery the MDX mice produced significantly less force compared to WT. While WT mice generated a similar amount of force which represents a lack of muscle damage.

Figure 6:
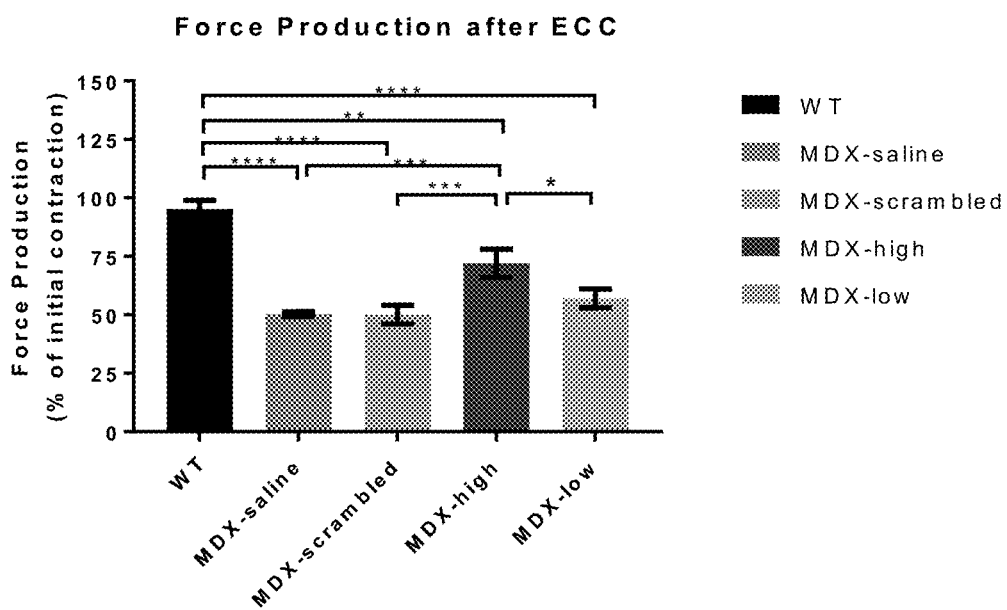
FIG. 6 is a graphical representation of data illustrating the force produced after eccentric muscle contraction. While MDX controls generated about 50% less force that the initial force produced, mice injected with high dose inhibitory oligonucleotide generated significantly more force, i.e., about 70% of the initial force produced.

FIG. 6 shows the eccentric muscle contraction force produced as a % of initial contraction+/−SEM. The MDX saline, scrambled and low dose antisense oligonucleotide generated ~50% less force than the initial force produced. Mice injected with high dose antisense oligonucleotide generated ~70% of the initial force produced. This is significantly less than a WT but significantly more than the saline, scrambled and low dose treated MDX mice.

Biochemical Blood Markers

Figure 7:
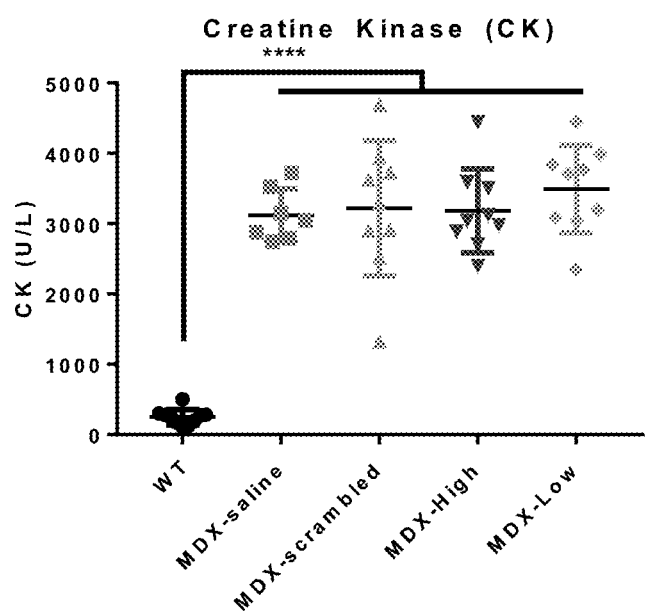
FIG. 7 is a graphical representation of data showing creatine kinase levels in the blood of WT and MDX-saline, scrambles and treated (High and Low dose) mice. A significant increase was seen in all MDX mice compared to wild type controls.

FIG. 7 shows the creatine kinase (CK) levels in the blood of WT and MDX-saline, scrambled and treated (High and Low) mice. The muscle CK levels (U/L) were measured in the blood of WT and MDX mice after 6 weeks of treatment. CK is a circulating protein that can be used as an indirect marker to assess muscle damage. A significant increase in circulating CK was observed in all MDX samples compared to WT, however no differences between treatments in the MDX groups were observed (FIG. 7).

Immune Cells in the Spleen: Reduction in CD49d Cell Surface Marker Expression

Oligonucleotide drugs administered to mice rapidly distribute from the blood to the tissues including to the primary and secondary lymphoid organs which contain white blood cells. The spleen, a lymphoid organ, was collected and cells isolated for flow cytometry analyses of the white blood cells. Various cell surface markers including the antisense oligonucleotide target cell surface molecule CD49d alpha chain of VLA-4 levels were assessed using fluorescently labelled antibodies that are excited by a laser to emit light at varying wavelengths. The CD49d positive white blood cell count was reduced in the spleen of mice treated with a high dose of antisense oligonucleotide to CD49d, ISIS 348574 (20 mg/kg s.c) compared to saline-control (data not shown).

TABLE 1

| TA Muscle physiology characteristics | | | | | |
|---|---|---|---|---|---|
| | WT | MDX-saline | MDX-scrambled | MDX-high | MDX-low |
| TA muscle mass (mg) (±SD) | 45.4 (±4.2) | 71.1 (±4.6)$^a$ | 68 (±7.4)$^a$ | 72.6 (±6.3)$^a$ | 71.2 (±4.5)$^a$ |
| Absolute Force (mN) (±SD) | 1542.1 (±161.7) | 1603.2 (±136.9) | 1549.8 (±224.5) | 1448.8 (±193.9) | 1484.9 (±278.1) |
| Specific Force (mN/mm2) (±SD) | 231 (±17.3) | 151.5 (±19.8)$^a$ | 161.8 (±25.0)$^{a,b}$ | 139.2 (±30.8)$^{a,b}$ | 145.7 (±24.8)$^a$ |
| Number of mice (n) | 12 | 12 | 12 | 12 | 12 |

$^a$significantly different from WT (P < 0.0001)
$^b$P = 0.0780

Many modifications are encompassed as known to those of skill in the art.

BIBLIOGRAPHY

Altschul et al., J. Mol. Biol. (1990) 215:403-410
Ausubel et al. (editors) Current Protocols in Molecular Biology, Supplement 47, John Wiley & Sons, New York, 1999
Colowick and Kaplan, eds., Methods In Enzymology, Academic Press, Inc.
Elbashir et al., Nature (2001a) 411:494-498
Elbashir et al., Genes Dev. (2001b) 15:188-200
Englisch et al., Angewandte Chemie, International Edition (1991) 30:613
Fire et al., Nature (1998) 391:806-811
Garton et al. The American Journal of Human Genetics 102, 845-857, 2018 Grounds MD, Cell. Mol. Life. Sci. 2008
Guo and Kempheus, Cell (1995) 81:611-620
Hogarth et al. Nature Communications 8:14143, 2017
Limmroth et al. Americal Academy of Neurology 83 11 Nov. 2014
Montgomery et al., Proc. Natl. Acad. Sci. USA. (1998) 95:15502-15507

Nielsen et al., Science (1991) 254, 1497-1500
Pane et al, PLOS One, 1-8 Jun. 20, 2018
Remington's Pharmaceutical Sciences (18$^{th}$ ed., Mack Easton, Pa. (1990),
Ricotti V, et al. (2016) Upper Limb Evaluation in Duchenne Muscular Dystrophy: Fat-Water Quantification by MRI, Muscle Force and Function Define Endpoints for Clinical Trials. PLoS ONE 11(9): e0162542. doi:10.1371/journal.
Rosenberg A S, Puig M, Nagaraju K, et al. Immune-mediated pathology in Duchenne muscular dystrophy. Sci Transl Med 2015, 7: 299rv4.
Tabara et al., Science (1998) 282:430-431
Tijsterman et al., Science (2002) 295:694-697
Timmons and Fire, Nature (1998) 395:854
Tuschl et al., Genes Dev. (1999) 13:3191-3197
Wan et al. Nucleic Acids Research 42 (22:13456-13468, 2014
Weir and Blackwell, eds., Handbook of Experimental Immunology, Vols. I-IV, Blackwell Scientific Publications, 1986
Zhang and Madden, Genome Res. (1997) 7:649-656
J. I. Kroschwitz (editor), The Concise Encyclopaedia of Polymer Science and Engineering, pages 858-859, John Wiley and Sons (1990)
S. Sanghvi, Chapter 15: Antisense Research and Applications, pages 289-302, S. T. Crooke, B. Lebleu (editors), CRC Press, 1993.

The invention claimed is:

1. A method for improving limb muscle function or strength or delaying decline in limb muscle function or strength in a subject with muscular dystrophy (MD), the method comprising periodically administering to the subject a pharmaceutical composition comprising a pharmaceutically acceptable carrier and a therapeutically effective amount of an oligonucleotide comprising the structure:

5'-$^{Me}C^{Me}$UG AGT $^{Me}$CTG TTT $^{Me}U^{Me}C^{Me}$C A$^{Me}$U$^{Me}$U $^{Me}C^{Me}$U-3' (SEQ ID NO: 1)

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}$C), or a pharmaceutically acceptable salt or stereoisomer thereof, for a time and under conditions sufficient to improve limb muscle function or strength in the subject; and wherein the therapeutically effective amount is 25 mg to 100 mg.

2. The method of claim 1, wherein the periodic administration is once or twice or three times per week or fortnight or month.

3. The method of claim 1, wherein the muscular dystrophy (MD) is selected from the group consisting of Duchenne muscular dystrophy (DMD), limb girdle muscular dystrophy (LGMD), Becker muscular dystrophy (BMD), congenital muscular dystrophy (CMD), fascioscapulohumeral, oculopharyngeal, Emery-Dreifuss, and distal muscular dystrophy.

4. The method of claim 3, wherein the muscular dystrophy (MD) involves a mutation in a dystrophin gene.

5. The method of claim 1, wherein the subject is diagnosed with Duchenne muscular dystrophy (DMD) and is ambulatory or non ambulatory.

6. The method of claim 1, wherein administration is in combination with corticosteroid treatment.

7. The method of claim 6, wherein corticosteroid treatment is administered at a standard daily dose of 0.75 mg/kg prednisolone or a standard daily dose of 0.9 mg/kg deflazacort.

8. The method of claim 1, wherein the therapeutically effective amount is once or twice weekly 25 mg or 50 mg dose.

9. The method of claim 1, wherein the therapeutically effective amount is once or twice weekly 0.4 to 1.5 mg/kg dose.

10. The method of claim 6, wherein the corticosteroid treatment is prednisolone administered at a dose 40% to 80% lower than a standard daily dose of 0.75 mg/kg or deflazacort administered at a dose 40% to 80% lower than a standard daily dose of 0.9 mg/kg.

11. The method of claim 6, wherein the corticosteroid treatment is prednisolone administered at a dose 40% to 70% lower than a standard daily dose of 0.75 mg/kg or deflazacort administered at a dose 40% to 70% lower than a standard daily dose of 0.9 mg/kg.

12. The method of claim 6, wherein the corticosteroid treatment is 10 to 40 mg of prednisolone or deflazacort.

13. The method of claim 6, wherein the corticosteroid treatment is 20 to 30 mg of prednisolone or deflazacort.

* * * * *